(12) United States Patent
Krueger

(10) Patent No.: US 10,099,030 B2
(45) Date of Patent: Oct. 16, 2018

(54) MECHANICAL AND FLUID SYSTEM AND METHOD FOR THE PREVENTION AND CONTROL OF MOTION SICKNESS, MOTION-INDUCED VISION SICKNESS, AND OTHER VARIANTS OF SPATIAL DISORIENTATION AND VERTIGO

(71) Applicant: Wesley W. O. Krueger, San Antonio, TX (US)

(72) Inventor: Wesley W. O. Krueger, San Antonio, TX (US)

(73) Assignee: IARMOURHOLDINGS, INC., San Antonio, TX (US)

( * ) Notice: Subject to any disclaimer, the term of this patent is extended or adjusted under 35 U.S.C. 154(b) by 434 days.

(21) Appl. No.: 14/736,132

(22) Filed: Jun. 10, 2015

(65) Prior Publication Data
US 2015/0273179 A1 Oct. 1, 2015

Related U.S. Application Data

(63) Continuation-in-part of application No. 14/020,450, filed on Sep. 6, 2013, now Pat. No. 9,080,868.

(51) Int. Cl.
*A61M 21/00* (2006.01)
*A61M 21/02* (2006.01)
(Continued)

(52) U.S. Cl.
CPC ............. *A61M 21/02* (2013.01); *G01C 9/02* (2013.01); *G01C 9/10* (2013.01); *G01C 9/12* (2013.01);
(Continued)

(58) Field of Classification Search
CPC ... G01C 9/10; G01C 9/16; G01C 9/20; G01C 9/005; A61M 2021/005; A61M 21/02; A61M 2021/0044
See application file for complete search history.

(56) References Cited

U.S. PATENT DOCUMENTS

| 1,576,260 A | 3/1926 | Waite |
| 3,487,549 A | 1/1970 | Engesser |

(Continued)

*Primary Examiner* — Christine H Matthews
(74) *Attorney, Agent, or Firm* — Kilpatrick Townsend & Stockton LLP

(57) ABSTRACT

A non-electronic head-worn system for providing visual inertial head orientation information to a person is disclosed. The system comprises a head-worn unit that displays at least one orientation reference symbol to the person wearing the unit wherein the orientation reference symbol stays in a fixed visual position for the person when the person's head changes orientation. The system comprises an optical element located in the optical path between the user's eye and the orientation reference symbol, such as a lens, mirror, a prism, a beam splitter, a retro-reflector, or any other device or medium that can change the appearance or apparent location of an image. The system further comprises a pitch indicator that gives visual pitch information to the person and/or a roll indicator that gives visual roll information to the person. The pitch indicator and the roll indicator are responsive to a pendulum, a rolling element, or a fluid in a reservoir. The pitch element and the roll element do not use electricity or electronics.

18 Claims, 22 Drawing Sheets

(51) Int. Cl.
    *G01C 9/02*       (2006.01)
    *G01C 9/12*       (2006.01)
    *G01C 9/28*       (2006.01)
    *G02C 11/00*      (2006.01)
    *G01C 9/10*       (2006.01)
    *G01C 9/16*       (2006.01)
    *G01C 9/20*       (2006.01)

(52) U.S. Cl.
    CPC ................ *G01C 9/16* (2013.01); *G01C 9/20* (2013.01); *G01C 9/28* (2013.01); *G02C 11/00* (2013.01); *A61M 2021/005* (2013.01); *A61M 2209/088* (2013.01)

(56) References Cited

U.S. PATENT DOCUMENTS

| | | |
|---|---|---|
| 3,871,104 A | 3/1975 | Underhill |
| 4,426,138 A | 1/1984 | Sheridan |
| 5,966,680 A | 10/1999 | Butnaru |
| 6,568,396 B1 | 5/2003 | Anthony |
| 6,783,237 B1 * | 8/2004 | Jeannin ................ G02C 5/001 351/158 |
| 6,932,090 B1 | 8/2005 | Reschke et al. |
| 7,490,611 B2 | 2/2009 | Bromwich |
| 9,080,868 B2 * | 7/2015 | Krueger ................ G01C 9/16 |
| 2009/0082831 A1 | 3/2009 | Paul et al. |
| 2011/0282130 A1 | 11/2011 | Krueger |
| 2012/0035430 A1 | 2/2012 | Roth |
| 2012/0134543 A1 | 5/2012 | Fedorovskaya et al. |
| 2012/0182206 A1 | 7/2012 | Cok et al. |
| 2014/0361976 A1 | 12/2014 | Osman et al. |
| 2014/0368539 A1 | 12/2014 | Yeh |

\* cited by examiner

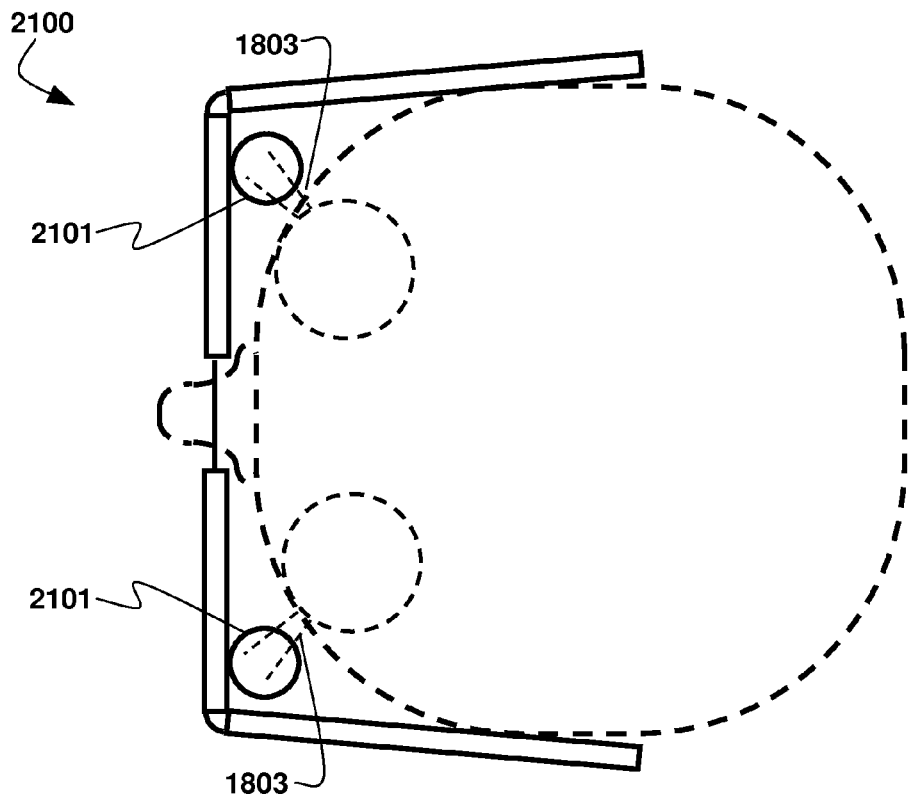
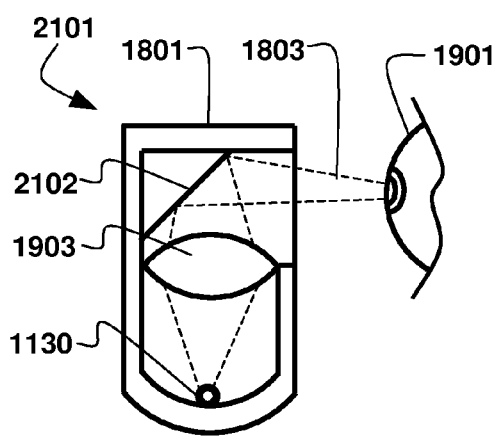 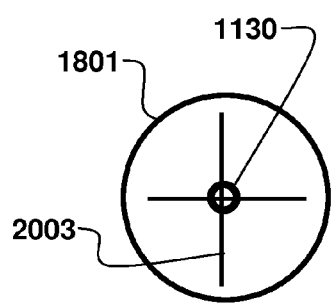
Fig. 21A
Fig. 21B
Fig. 21C

MECHANICAL AND FLUID SYSTEM AND METHOD FOR THE PREVENTION AND CONTROL OF MOTION SICKNESS, MOTION-INDUCED VISION SICKNESS, AND OTHER VARIANTS OF SPATIAL DISORIENTATION AND VERTIGO

CROSS-REFERENCE TO RELATED APPLICATIONS

This application is a continuation-in-part of U.S. application Ser. No. 14/020,450 filed Sep. 6, 2013, which is hereby incorporated by reference in its entirety.

BACKGROUND

The present invention generally relates to head worn devices and methods for mitigating or preventing motion sickness. Motion sickness can include vertigo, simulation sickness, gaming sickness, spatial disorientation, dizziness, vision induced motion sickness or vection induced motion sickness in 2-D, 3-D, or 4-D environments, including the viewing of displays such as with operation of remote devices, in simulators, medical imaging, surgical training or operations, virtual environments, scientific visualization, space use, or gaming. The head worn devices can be attachable and detachable from another device attached to the head, such as a helmet or glasses; the head worn devices can be integrated into another device attached to the head, such as a helmet or glasses; or the head word devices can be standalone devices attached to the user's head. Mitigation and prevention of motion sickness more specifically relates to the use of a visual reference to prevent conflicting sensory mismatch between the visual, proprioceptive, and inner ear senses. The visual reference may be controlled through a mechanical or fluid system responsive to gravitational forces. The prevention and control of motion-related sickness and spatial disorientation can minimize symptoms of nausea, vomiting, and factors that compromise human performance in motion-related environments.

Motion Sickness occurs because of the mismatched sensation with what is seen compared to what is felt and what is perceived in the inner ear. There are many different types of provocative motion environments that can induce motion sickness, motion-induced vision sickness, and other variants of spatial disorientation and vertigo. Often these provocative environments are intensely stimulating but for many people with motion intolerance, the provocative motion environment may be subtle. Provocative motion environments can be associated with locomotion such as ships, hovercraft, aircraft, automobiles, and trains. The complex accelerations generated by fairground amusements, such as swings, roundabouts (merry-go-rounds), roller coasters and so on, can be highly provocative. Astronauts/cosmonauts can suffer from motion sickness (space-motion sickness) when they first make head movements in the abnormal force environment (weightlessness) of orbital flight. Provocative motion environments can also be experienced by moving visual stimuli, without any physical motion of the observer. Typical examples of visually stimulating environments include participating in virtual reality platforms or systems. Virtual reality (VR), Augmented Reality (AR), Multi-Dimensional (MD) and Synthetic environmental systems encompasses a set of technologies that place the user in a computer-generated, three-dimensional environment and all can encompass a provocative motion environment for the user. Augmented reality mixes the physical with the virtual, layering computer-generated objects and information onto the real world. These types of environments can create a VR experience that truly fools the brain. The feeling of experiencing reality while in a VR, AR, MD and synthetic systems is a very profound one, as the brain interprets sensory data as though actually experiencing an event. For many using these platform systems, the result is visually induced motion sickness. Simulator sickness is another example of motion sickness, and simulator sickness in virtual reality environments (VRE) has become an important issue. Most provocative motion environments cause three distinct, but possibly related, responses: reflexive eye movements (EM), sensory conflict (SC), and postural instability (PS). A provocative motion stimulating environment can be defined as being immersed in an environment where the user can experience vestibular stimulation, (such as with vehicular motion), visual stimulation (such as with simulator, VR, AR, MD, or other synthetic visual systems), postural or proprioceptive disturbances (such as with experiencing vertical vibrations with frequencies between 0.16-2.0 Hz) and even with sequentially based low frequency auditory signals. Some examples of provocative motion environments include vehicle use, an AR (augmented reality environment), a multi-dimensional environment, a synthetic or computer generated synthetic environment, and/or a visual induced environment, such as watching motion while the user is motionless.

Mismatched sensation of what is seen compared to what is felt and what is perceived in the inner ear can occur any time when the brain perceives that the body is in motion (through signals originating in the labyrinth and transmitted to the brain by the vestibular nerve), but the motion sensed does not match what the eye can see and verify. For example, a passenger traveling along a winding road in a vehicle experiences linear and angular accelerations as the vehicle travels around a curve. The response of the vestibular sensing system to the acceleration caused by the motion of the vehicle will not match the visual perception unless the person is constantly viewing the road so that the perception of the person's inner ear matches that which is visually perceived. Passengers in a vehicle who are doing other tasks such as reading will have a visual perception that does not match the senses of their inner ear and may experience symptoms of motion sickness. Additionally the sensory mismatch can occur when the eye perceives motion, but the labyrinth does not provide confirming signals to the brain (such as watching a rocking boat while motionless). It can affect anyone and depending on the degree of provocation can be quite disabling. Balance receptors respond to gravity, velocity and changes in velocity. Some of the inner ear receptors sense linear or tilt motion and other sense rotational movement.

Motion Sickness, spatial disorientation and vertigo have been acknowledged as a widespread problem, affecting a significant portion of world population to varying degrees. Researchers report that up to 60% of the population has some motion intolerance. It has been reported that motion sickness affects nearly one third of all people who travel by land, sea, or air. Individuals are affected daily by motion sickness and spatial disorientation while riding in automobiles, trains, buses, planes or other transport. The Greeks provided the first written historical account of motion sickness. The Roman Cicero claimed he would rather be killed in battle than suffer the tortures of nausea maxis. Motion sickness has even been used as a form of punishment. One of the world's most famous mariners, Admiral Lord Nelson reportedly never adapted to motion sickness. Napoleon's General Carbuccia refused to use camels for Napoleon's army, because of the issues with motion (2) Even Lawrence of Arabia is reported to have experienced Camel sickness.

It is also known that some people are more susceptible than others; for example, women are more sensitive to motion than men by a ratio of about 5:3. Some are more susceptible due to physical reasons such as age. Studies show a significant genetic contribution to a propensity to motion sickness. It has been well observed that poor ventilation, bad odors, smoking, eating large fatty meals and alcohol can make motion sickness more pronounced. Susceptibility to motion sickness begins at about age two, and for most will peak in adolescence and decline gradually. However, many adults remain highly sensitive caused by any motion, particularly when combined with either an absence of a visual reference or to significant levels of visual stimuli. In fact, a provocative visual stimulus has been shown to be the most influential cause of motion sickness symptoms. Reading in a moving vehicle, abruptly moving the head (such as looking down) while a vehicle is moving can provoke symptoms. Fear, anxiety and other psychological factors can contribute to the onset of motion sickness. Some people can get sick just thinking about an upcoming trip or flight.

For those who experience the symptoms, the result is often disabling, with nausea, vomiting, sweating, and unsteadiness, while feeling cold, clammy and disorientated. In addition, the term "sopite syndrome" was coined to refer to the apathy, passivity, and lack of concentration characteristic of motion sickness.

Of the 12.6 million passengers who cruise annually, an estimated 20% or more become seasick. The occurrence of motion sickness can approach 100% in cruise ship passengers on rough seas. Seasickness, a common form of motion sickness, is also frequent among naval personnel, where 60% to 90% percent of inexperienced sailors can suffer from seasickness. Experienced crewmembers are not immune. Up to 60% of experienced crewmembers have been affected in these conditions. This becomes a major problem in modern seamanship in which small crews are responsible for the operation of sensitive and sophisticated equipment. During the invasion of Normandy, in World War II, the seas were reportedly very high causing the landing crafts to pitch and yaw, like a kite in a windstorm. The soldiers were lying and sitting in flat bottomed crafts and were using huge buckets for vomiting and urinating, which soon overflowed after boarding. As thousands of men were lying in the vomit, urine and rain they debarked in a state of terror, which was compounded by their symptoms of seasickness, and attempted to perform at a high level in order to survive in combat. Many of these soldiers had to overcome the most debilitating effects of motion sickness to survive. There are additional volumes of data that document the severe effect of motion sickness on human performance of even basic tasks.

Spatial disorientation and motion sickness are significant problems in aviation. In motion provocative environments, spatial disorientation and motion sickness cause not only a loss in human performance (affecting cognitive and motor skills), but also a loss of expensive aircraft and human life. Thousands of deaths have been attributed to aviation accidents caused by being spatially disoriented. In a review of aviation mishaps from 1987-1997 by the Aviation Safety Foundation of the Aircraft Owners and Pilots Association, there was an average of one fatal SD accident every 11 days in the United States. These accidents have resulted in a fatality rate of 91% in the General Aviation (GA) community and a 69% fatality rate in the U.S. Military. There are over 650,000 civilian pilots in the United States alone. Non-instrument rated pilots who fly into the clouds historically have 178 seconds before ground impact. The death of John F. Kennedy Jr. was an example of a spatial disorientation accident and unknown to many were thirty other reported crashes that same day, with at least one other due to spatial disorientation. According to FAA statistics, SD and loss of situational awareness causes 15%-17% of fatal general aviation crashes annually. More significantly, 9 out 10 SD mishaps result in a fatality. From 1980-2000, the USAF experienced 1,087 aviation fatalities with over 14% (172) directly attributed to SD at a cost of over $1.54B. A recent study has shown that almost 90-100% of aircrews have reported at least one incidence of spatial disorientation (SD) during their flying careers. SD accounted for 11-14% of USAF mishaps and a mishap fatality rate of 69%, with risk of SD significantly increased in helicopters and fighter/attack aircraft and at night. The most frequent experienced SD episodes are "leans" (92%), loss of horizon due to atmospheric conditions (82%), misleading altitude cues (79%), sloping horizon (75%), and SD arising from distraction (66%). The Air Force Safety Center FY 93-02 mishap analysis reported that Class A mishaps resulted in 243 destroyed aircraft, 310 fatalities, and an economic loss of $6.23 billion. Airsickness has also been identified as a flight training issue. A motion sickness history questionnaire obtained from student pilots in the Air Force revealed an incidence of airsickness of 50%. In a questionnaire to B-1 and B-52 bomber crewmembers, it was reported to be a frequent occurrence among non-pilots in both aircraft, and experienced crewmembers were more likely to report an impact on their duties.

Space motion sickness is experienced by 60%-80% of astronauts during the first 2-3 days in micro gravity and by a similar proportion during their first few days after return to Earth. Up to 90% of astronauts experienced spatial disorientation during reentry and landing of the shuttle, with prevalence proportional to the length of the mission. Exposure to micro gravity rearranges the relationships among signals from visual, skin, joint, muscle, and vestibular receptors. Congruence between vestibular signals and those from other receptors, as well as between the vestibular otolith and semicircular canal receptors, is disrupted by the absence of gravity. This lack of congruence between sensory exposure to provocative real or apparent motion leads to the progressive cardinal symptoms of terrestrial motion sickness. Space motion sickness may vary slightly with flushing more common than pallor, stomach awareness, malaise, loss of appetite, and sudden vomiting, often without prodromal nausea. The only remedy to space motion sickness at this moment is drug therapy while stationed in space, a decidedly non-optimal solution. Additionally during training for space flight students aboard the zero-G flight simulator routinely experience motion sickness. When people go up into space, many will immediately get space sickness, according to NASA's Biomedical Research and Countermeasures Program. While a few astronauts are apparently immune, most can experience symptoms ranging from mild headaches to vertigo and nausea. In extreme cases prolonged vomiting can make an astronaut dehydrated and malnourished. Motion sickness remains a persistent problem in space flight. Proposed etiological factors in the elicitation of space motion sickness include fluid shifts, head movements, visual orientation illusions, Coriolis cross-coupling stimulation, and otolith asymmetries. Space sickness relieves itself after about 3 days, for some although individual astronauts and cosmonauts may have a relapse at any time during their mission and continue to take medication, which can alter their cognitive and motor function. For those personnel in sub-orbital flights performing a research job or experiment for a client, they cannot afford to be sick or disoriented or distracted. They have four to five minutes on a sub-orbital flight to get a job done. If afflicted with space sickness human performance is compromised. In the private space tourism companies it is a known fact that passengers are very likely to have space sickness, or its more scientific name, Space Adaptation Syndrome (SAS). Even with medication, most astronauts experience it when they go to space to varying degrees, from mild nausea or a headache to vomiting. SAS is a main reason that extra-vehicular activities (EVA) outside of the space shuttle are done only after a few days in space, as vomiting inside a space suit is lethal. Some astronauts who show an exceptional tolerance to motion sickness when flying jets suffer the worst symptoms upon arriving in space. Astronauts returning from extend space flights routinely have to learn to reorient themselves in the terrestrial environment. Motor and cognitive skills are often observed to be severely degraded during the re-acclimation period. This is due to the sudden reintroduction of gravitational cues and stimulus of proprioceptors. The time needed to re-acclimate to the terrestrial environment is about three days per week in space.

Vestibular disorders affect an estimated 20% of the general population. 90 million Americans (42% of the population) will complain of dizziness at least once during their lifetimes, and 80% of these complaints will have a vestibular component. There are more than 10 million physician visits annually for dizziness or balance complaints (Source: National Balance Centers/Vestibular Disorders Association), with a cost of greater than one billion dollars per year. Postural control requires a complex interaction of visual and proprioceptive sensory inputs providing external orientation reference frames while the internal reference frame is provided by the vestibular system. Persistent vestibular dysfunction can occur following a variety of insults to the vestibular system, including infections, ototoxicity, trauma, chronic ear pathology, tumors, Meniere's disease, surgery and other idiopathic causes. Acoustic tumor surgery and vestibular nerve section, performed for disabling vertigo in patients with Meniere's disease, usually result in rapid compensation. However some patients, particularly non-Meniere's disease patients, have a prolonged period of unsteadiness without compensation for a long period of time. The resulting disability can be devastating. It has also been shown that postural instability precedes motion sickness with provocative visual stimuli. All these vestibular impairments cause disequilibrium, blurred vision, disorientation, and vertigo, which in turn cause dysfunction in many activities of daily living and in social interactions that traditional medical treatments may not address.

Medical rehabilitation, overcoming chronic illness, recovery from surgery, and recovery from trauma represent additional applications. Presently, 10 million patients receive balance (vertigo) medical rehabilitation therapy costing $1 billion annually. Reasons for treatment are due to disease affecting the vestibular organs, rehabilitation from surgery on the balance organs, recovery from trauma to the head and rehabilitation in patients learning to use prosthetics in the lower extremities. Clinical tests conducted by the inventor funded by the National Institutes of Health (NIH) resulted in 96% effectiveness in resolving balance issues associated with these various maladies. Regarding overcoming chronic illness, many patients with the NIH test group with chronic balance disorders were able to return to functionality after enduring years of other ineffective treatments. The visual display reduced the average number of clinical visits from 25 rehabilitation treatments to 5 and in several cases proved to be the only effective treatment the patient had ever experienced. Regarding recovery from surgery, within the NIGH test group, the visual display proved to reduce the average number of clinical visits from 25 rehabilitation treatments to 5 and in several cases proved to be the only treatment effective. Regarding recovery from trauma, head trauma and injury to the inner ear often result in temporary balance problems. The loss of proprioception with injuries to extremities can also result in loss of balance. In tests the visual display greatly shortened rehabilitation and recovery times and in some cases was the only treatment effective to aid recovery due to head trauma, vestibular injury and limb injury. Regarding rehabilitation using prosthetics to lower extremities, physicians associated with the US Army Center for the Intrepid, based at Brook Army Medical Center in San Antonio Tex. report that many soldiers who have suffered injury to the lower extremities or amputation have balance issue while learning to use prosthetics. This is due in part to loss of proprioception inputs associated with the loss of the limbs and new weight distribution associated with the prosthetics. It is hypothesized our technology will greatly shorten rehabilitation time by providing strong visual cues to offset the loss of sense of touch due to limb loss and aid balance while learning to use the new limbs.

Simulation sickness, or simulator sickness, is a condition where a person exhibits symptoms similar to motion sickness caused by playing computer/simulation/video games. Simulation sickness or gaming sickness cause symptoms quite similar to that of motion sickness, and can range from headache, drowsiness, nausea, dizziness, vomiting and sweating. Research done at the University of Minnesota had students play Halo for less than an hour, and found that up to 50 percent felt sick afterwards. In a study conducted by U.S. Army Research Institute for the Behavioral and Social Sciences in a report published May 1995 titled "Technical Report 1027—Simulator Sickness in Virtual Environments", out of 742 pilot exposures from 11 military flight simulators, "approximately half of the pilots (334) reported post-effects of some kind: 250 (34%) reported that symptoms dissipated in less than 1 hour, 44 (6%) reported that symptoms lasted longer than 4 hours, and 28 (4%) reported that symptoms lasted longer than 6 hours. There were also 4 (1%) reported cases of spontaneously occurring flashbacks." Simulator sickness is another example of motion sickness, and many military pilots have reported at least one symptom following simulator exposure. In a study of Coast Guard aviators undergoing flight simulator testing, 64% reported adverse symptoms during the first simulator flight and 39% did so during the last flight. 36% of pilots reported motion sickness when training on a Blackhawk flight simulator.

More recently, simulator sickness in virtual environments (VE) has become an important issue. Virtual reality is already a popular technology for entertainment purposes, and both the U.S. Army and Navy are interested in the training applications of virtual environments. However, some users of VE experience discomfort during, and sometimes after, a session in a simulated environment, in equivalent fashion to simulator sickness already noted for flight and driving simulators. Similarly, in casual gaming, a number of modern electronic games feature a virtual control interface. These displays are often not see-through and present highly motion provocative visual displays.

Motion sickness due to virtual reality is very similar to simulation sickness and motion sickness due to films. In virtual reality, however, the effect is made more acute as all external reference points are blocked from vision, the simulated images are three-dimensional and in some cases stereo sound that may also give a sense of motion. The world's most advanced simulator, the NADS-1, located at the National Advanced Driving Simulator, is capable of accurately stimulating the vestibular system with a 360-degree horizontal field of view and 13 degree of freedom motion base. Prior studies have shown that exposure to rotational motions in a virtual environment can cause significant increases in nausea and other symptoms of motion sickness. Counter Vertigo in Virtual Pilot Vehicle Interface. Operators of unmanned aerial systems (UAS) routinely experience spatial disorientation due to limited visual cues in sensor control displays. Further, experiments using a virtual pilot vehicle control interface, where the pilot controlled the UAS based on visual cues derived directly through sensors (placing the point of view on the nose of the aircraft) versus via CRT control displays led to cases of SD and motion sickness. It is believed our technology will prevent SD/MS in both UAS PVI environments.

Vision Induced Motion Sickness, such as the motion sickness due to films and other video is a type of sickness, is particularly prevalent when susceptible people are watching films on large screens such as IMAX but may also occur in regular format theaters or even when watching TV. For the sake of novelty, IMAX and other panoramic type theaters often show dramatic motions such as flying over a landscape or riding a roller coaster. There is little way to prevent this type of motion sickness except to close one's eyes during such scenes or to avoid such movies. In these cases, motion is detected by the visual system and hence the motion is seen, but no motion or little motion is sensed by the vestibular system. Motion sickness arising from such situations has been referred to as Visually Induced Motion Sickness (VIMS). Movie-induced motion sickness has become more prevalent due to new cinematographic techniques. For example, there are claims that "The Hobbit: An Unexpected Journey" has caused motion sickness and nausea among viewers. The film having been shot using 3-D and new 48 fps (frames per second) technology, double the standard rate of 24 fps that has been used to shoot films since 1927. Additionally, in regular format theaters, another example of a movie that caused motion sickness in many people was The Blair Witch Project. Theaters warned patrons of its possible nauseating effects, cautioning pregnant women in particular. Blair Witch was filmed with a handheld camcorder, which was subjected to considerably more motion than the average movie camera. Home movies, often filmed with a hand-held camera, also tend to cause motion sickness in those that view them. The cameraperson rarely notices this during filming since his/her sense of motion matches the motion seen through the camera viewfinder. Those who view the film afterward only see the movement, which may be considerable, without any sense of movement. Using the zoom function seems to contribute to motion sickness as well as zooming is not a normal function of the eye. The use of a tripod or a camcorder with image stabilization technology while filming can minimize this effect. 55% of people who watch 3D movies have MS. Following the market expansion of movies filmed with three-dimensional (e.g. 3D) technology and televisions equipped with 3D displays for the home entertainment, there has been an increasing concern about possible side effects on spectators. It has been suggested that the viewing of 3D stereoscopic stimuli can cause vision disorders to manifest in previously asymptomatic individuals. The prevalence of health outcomes on 3D movie spectators appears to be increasing in domestic environments.

Research on professional exposures to virtual reality systems, vehicle simulators, and stereoscopic displays have reported that several adverse health effects can be induced by viewing motion images, including visual fatigue (also termed asthenopia), or eyestrain, vection induced motion sickness and visually induced motion sickness (VIMS). Symptoms of visual fatigue induced by images comprise eye discomfort and tiredness, pain and sore around the eyes, dry or watery eyes, headaches and visual distortions such as blurred and double visions, and difficult in focusing. The main physiological mechanism involved with the onset of visual fatigue concerns the intense eye accommodation activity of 3D movie viewers, such as focusing and converging. It has been argued that eye focus cues (accommodation and blur in the retinal image) target the depth of the display (or of the movie screen) instead of the displayed scene, generating unnatural depth perception. Additionally, uncoupling between vergence and accommodation affects the binocular fusion of the image. Both processes may generate visual fatigue in susceptible individuals. In addition to symptoms of visual fatigue, viewers of 3D may experience nausea (nausea, increased salivation, sweating) and disorientation (dizziness, vertigo, fullness of head). Those symptoms are indicative of VIMS, a condition that may onset during or after viewing dynamic images while being physically still, when images induces in the stationary spectator a sense of vection (i.e. illusion of self-movement). The most accepted explanation for VIMS is the classical conflict theory based on the mismatch between the visual, the proprioceptive and the vestibular stimuli. In this case, the visual system feels vection while the vestibular and proprioceptive systems do not transmit signals consistent with motion. Notably, although VIMS and visual fatigue are different conditions, they probably share some common biological mechanisms.

The specific disturbance deriving from viewing 3D movies has been named "3D vision syndrome" but the relative occurrence of different symptoms in spectators and the individual characteristics that make some individuals more susceptible than others still remain to be described. Previous research showed that occurrence of self-reported symptoms in young healthy adults during or immediately after watching a 3D movie may be high, although often quickly disappearing once they finished viewing. Factors reported to be associated with VIMS can be categorized into (i) factors associated with the visual stimuli provided to viewers, (ii) factors associated with the position from where the viewers are watching the movie and (iii) the psychophysiological conditions of the viewers. Examples reported in literature include (but are not limited to): the characteristics of the (moving) images (e.g. the optic flow) such as the earth axis along which the visual field is made rotating, the amplitude of the field of view, the display angle, the feeling of immersion or presence, the co-presence of vection, the display types, postural instability, habituation, age, gender, and anxiety levels of viewers. Interactions and additive effects among factors may also be present, making difficult to predict the final outcome (if a given individual will or will not suffer VIMS).

Earlier experiences of visual discomfort observed in 3D display viewers led to the hypothesis that the conflict between vergence and accommodation stimuli is the cause of such visual discomfort. Controlled experimental conditions in which the effect of the vergence-focal conflict on visual fatigue could be isolated from other variables confirmed such explanation. Additionally, it has been argued that 2D movie viewers tend to focus at the actors while the eye movement patterns of 3D viewers are more widely distributed to other targets such as complex stereoscopic structures and objects nearer than the actors. This behavior might increase the vergence-accommodation mismatch, increasing the visual stress on 3D spectators. The higher intensity of visual symptoms when participants were exposed to the 3D movie compared to the 2D movie observed in our study could be taken as a large-scale evidence of such hypothesis. Possibly, a partially different mechanism is involved in the onset of nausea and disorientation related symptoms. Nausea, dizziness and vertigo are connected to vestibular disturbance and the visual—vestibular interactions and the classical sensory conflict theory can explain the onset of symptoms in susceptible individuals. The public health relevance of VIMS was raised some years ago in Japan when 36 (out of 294) high school students were hospitalized for motion sickness after watching a movie characterized by unexpected whole image motion and vibration (the so called Matsue movie sickness incident). A previous multivariate analysis suggested that seeing a 3D movie increases the simulator sickness questionnaire (SSQ) scores. Besides the exposure to 3D, significant predictors of higher SSQ total score were car sickness and headache after adjusting for gender, age, self-reported anxiety level, attention to the movie and show time. The use of glasses or contact lenses does not seem to increase the risk of raising SSQ scores. Women with a history of frequent headache, carsickness (and possibly dizziness, which is correlated with the above mentioned variables) may be more susceptible to VIMS than others. The relationships between motion sickness, vertigo, dizziness, and migraine is well documented and 3D movies may interact with these conditions to produce more symptoms than 2D movies.

Clearly viewing 3D movies can increase rating of nausea, oculomotor and disorientation. Analogous to riding a roller coaster, for most individuals the increases in symptoms is part of the 3D experience and enjoyment and these experiences is not necessarily an adverse health consequence. However, some viewers will have responses that in other contexts might be unpleasant. In particular, women with susceptible visual-vestibular system may have more symptoms when watching 3D movies. Individual variability of the 3D exposure including the length of the movie, the angle of view and the pre exposure baseline conditions are potential predictors of visual discomfort that may warrant future investigation. As noted by others, 3D viewing may increase task burdens for the visual system, and susceptible individuals may develop a "3D vision syndrome". Due to increasing commercial releases of 3D movies and displays for home and professional use it is likely that more people will complain about these symptoms.

The worldwide increasing popularity of commercial movies showing stereoscopic (e.g. three dimensional—3D motion images is documented by the fact that 3D releases are generating more revenues than the same movie released in 2D. In parallel with the expansion of digital 3D cinema systems, several consumer-electronics manufacturers released 3D televisions and displays for the home entertainment. For example, more than 300 3D videogames are already available for computers and consoles. Stereoscopic displays are becoming also very important for no leisure applications such as vision research, operation of remote devices, medical imaging, surgical training, scientific visualization, virtual prototyping, and many others. In the near future, it is predictable that more and more people will pass increased portion of time (either leisure or work time) viewing 3D motion images, raising concern about the 3D image safety and possible adverse side effects on end users.

There are concerns about possible adverse effects of watching novel visual images and experience of VR, such as photosensitive seizures, visually induced motion sickness (VIMS) and eyestrain. In particular, when a patient watches an image changed based on real-time information of his head-position, which is sometimes used in VR system, there is a possibility that he watches unexpected images, such as upside-down or rotating, and then he feels VIMS. Since almost all users of the rehabilitation system are aged and/or physically weak, mental or physical stress on them caused by VIMS is typically greater than on healthy users.

Stereoscopic three-dimensional (3D) displays and the viewing content are designed to heighten a sense of immersion and presence for viewers. As manufacturers increasingly offer 3D TV models and 3D TV programming content and commercial movies are made available to viewers at home, there is an increasing concern about visual, ocular, and physical discomfort reported by some 3D viewers. The commonly held explanation of visual symptoms in 3D viewing is that it stimulates a different vergence and accommodative demand than encountered in real 3D. The 3D displays provide stereoscopic visual stimulation by projecting separate images to each eye. Each image is a view of the scene from a slightly different angle, thereby simulating the different views of the eyes in a real scene. Stereoscopic depth provides relative depth information; i.e. it informs the viewer about the relative (not absolute) distances of objects with respect to one another. 4D/5D Theatre Technology: In recent years, 3D viewing has been accompanied with synchronization of some special effects installed in the theatres. When it rains in the movie, the audience also experiences the same. When there's lightening in the movie, the same happens in the theatre. Other effects include wind, fog, smell, sensation etc. These are called 4D effects. Theatres with 3D viewing, 4D effects and some seat movements are called 4D theatres. In cases of 5D theatres, seats move in synchronization with motion in the movie thus providing immersive experience to the audiences. For this at least six—directional seat movements are required: left and right rolls; forward and backward tilts; and up and down movements. These theatres show an excellent integration of 3D technology, audio, motion synchronization and multiple special effects using specialized software. For synchronization, using special software, movies and seat motion is pre-programmed.

Rotating devices such as centrifuges used in astronaut training and amusement park rides such as the Rotor, Mission: Space and the Gravitron can cause motion sickness in many people. While the interior of the centrifuge does not appear to move, one will experience a sense of movement. In addition, centrifugal force can cause the vestibular system to give one the sense that downward is in the direction away from the center of the centrifuge rather than the true downward direction. When one spins and stops suddenly, fluid in the inner ear continues to rotate causing a sense of continued spinning while one's visual system no longer detects motion.

There have been many theories about the cause of motion sickness, spatial disorientation and vertigo. Currently, the sensory conflict theory appears to be the dominant theory favored by researchers in that the majority of investigators agree that it is not solely the movement or movement stimulus that results in motion sickness, but rather a conflict in movement information detected by the different sensory modalities of the inner ear, vision, and proprioception. A conflict of visual and vestibular (inner ear) information, as it relates to postural control and visual stabilization, is certainly a critical factor. Investigators now also agree that it is primarily an incongruence of visual and vestibular sensory information regarding movement and orientation that results in motion sickness. Incongruence between the semicircular canals and the otolithic organ input has also been implicated as the provocative stimulus in seasickness and in the onset of motion sickness associated with weightlessness. Another contributing factor which may trigger susceptibility to motion sickness may be the mass size differences of the utricular otoconia between the left and right sides in some people, as seen in fish.

Within the sensory conflict concept has arisen an "incongruence in the visual system" theory, which can be called a Velocity Storage Theory. The vestibular nerve communicates head velocity and estimates of angular displacements require further central nervous system processing (i.e. integration). There is some inconsistency between velocity-based ocular studies and displacement-based perceptual studies. Most oculographic studies of vestibular function are based on measurements of the slow phase velocity of the eye. If a monkey or man is rotated at constant velocity in the dark, the velocity of the slow phase of the nystagmus decays exponentially with a time constant of Fifteen to Twenty seconds (15-20 sec). Direct recordings of the vestibular nerve in monkeys have shown the head velocity signal, transmitted by the vestibular nerve, has a time constant of decay of only Seven to Ten (7-10 sec). The duration of the eye velocity curve (i.e. a nystagmus response) is therefore longer, outlasting the sensation or perception curve. The perception of angular velocity is based on signals subserved by the brainstem velocity storage system. Thus the head velocity signal appears to be stored in the brain and then released onto ocular motor neurons for the generation of nystagmus. Brainstem circuits in the vicinity of the vestibular nuclei, behaving as mathematical integrators, are thought to mediate this storage process. There is evidence that motion sickness is generated through this velocity storage and can be reduced by reducing the angular vestibular ocular reflex time constant. Others support a multi-factor explanation of motion sickness, involving both sensory conflict and eye movement.

Ordinarily, eye movements prevent slip of images upon the retina from exceeding about 4 degrees per second. If retinal image velocity (RIV), commonly called, "retinal slip," exceeds 4 degrees per second, then visual acuity begins to decline and oscillopsia (an illusory movement of the stationary world) may result. Pursuit eye movements allow primates to follow moving objects with the eyes. When a target of interest starts to move, after a latency period of 120 ms, the eye accelerates smoothly in the direction of target motion to reduce the error between eye velocity and target velocity, i.e., retinal slip. Eye acceleration increases with the retinal slip and saturates at a value between 200 and 400°/s2 for non-periodic tracking in primates. In the middle of this acceleration period, a "catch-up" saccade is generated to reduce the error between eye and target positions that accumulated during the latency period. The catch-up saccade brings the image of the target on the region of the retina where visual acuity is the highest, the fovea. In primates, smooth pursuit gain, the ratio of eye velocity to target velocity, is close to unity. This indicates that at the end of the acceleration period, eye velocity almost perfectly matches target velocity. The period during which eye velocity matches target velocity is often referred to as steady-state pursuit. During steady-state pursuit in primates, eye velocity oscillates around a mean value. The frequency of this oscillation varies between 3.8 and 6 Hz and could reflect the delays inherent in the operation of a visual feedback loop. Retinal image slip promoted by fixational eye movements prevents image fading in central vision. However, in the periphery a higher amount of movement is necessary to prevent this fading. Even when the eye is fixating a point target it is not totally motionless because fixational eye movements keep it moving incessantly. There are three types of fixational eye movements: tremor, drift, and microsaccades. Tremor is an aperiodic, wave-like motion with velocities of approximately 20 minutes of arc/sec and amplitude smaller than the diameter of a foveal cone. Drift movements occur simultaneously with tremor and are larger and slower than tremor, with velocities in the order of 4 minutes of arc/sec and mean amplitudes of around 2-5 minutes of arc. This amplitude corresponds to a movement of the retinal image across a dozen photoreceptors. Fixational microsaccades, also called 'flicks' in early studies, are small and fast eye movements that occur during voluntary fixation. Typically with peak velocities above 600 minutes of arc/sec, their amplitude ranges from 1 to 120 minutes of arc and they carry the retinal image across a width corresponding to several dozen to several hundred photoreceptors.

Despite this incessant retinal motion, images are perceived as static and clear. The visual system has mechanisms to deal with movement and the eventual blur resultant from the retinal image slip caused by fixational eye movements. These mechanisms fail when the amount of movement is above their capacity of neutralization. In these conditions, the image is perceived as blurred due to motion smear. An immediate consequence of blur is a diminution of resolution. Gaze control in various conditions is important, since retinal slip deteriorates the perception of 3-D shape of visual stimuli. Several studies have shown that visual perception of 3-D shape is better for actively moving observers than for passive observers watching a moving object. When a stationary viewer is watching compelling moving scene, he or she can report sensation of self-motion illusion (called vection). Vection has been found to be correlated with levels of visual induced motion sickness (VIMS) and postural status. The correlation between vection and VIMS is consistent with the sensory conflict theory because sickness is generated in a sensory conflict situation where a person is reporting illusion of self-motion while remain physically stationary. The correlation between vection and VIMS has led to the term "vection induced motion sickness". One theory linking VIMS with inappropriate eye movements is consistent with the findings that suppression of eye movements by fixation can significantly reduce levels of VIMS. It has been hypothesized that the afferent signals in the ocular muscles will trigger vagal nuclei, resulting in a range of sickness symptoms associated with the autonomous nervous systems—the nystagmus theory. Because eye movements follow foveal stimulation and vection follows peripheral stimulation, the nystagmus theory indicates that in the presence of foveal stimulation, sickness will correlate with eye movements but not necessarily with vection. Since then, there have been competing studies reporting the decoupling between vection and VIMS as well as coupling between vection and VIMS. Some have felt that vection and motion sickness can be distinct phenomena and have further described Optokinetic stimulation generating circular-vection, and vection generated during a simulation of forward motion in a car as linear vection. In a prior study using an Optokinetic drum with this technology it was seen that both vection scores and simulator sickness scores were statistically significantly lower than when the technology was not used.

Eye fixation has consistently been shown to significantly reduce levels of visually induced motion sickness (VIMS). The common belief is that the reduction in VIMS is associated with the suppression of eye movement. One study proposed an alternative theory to associate the reduction of VIMS due to eye fixation with the increases in peripheral retinal slip velocity. Results showed that when participants were watching striped patterns rotating at 7 dps (degrees per second), eye fixation significantly increased the peripheral retinal slip velocity from about 2.6 dps to 7 dps and but failed to cause a significant change in the average rated levels of VIMS. However, in the same study, increasing the peripheral retinal slip velocity of moving patterns from 2.6 dps to 35 dps in the presence of OKN significantly increased the rated levels of nausea from 2.1 (mild unpleasant symptom) to 3.6 (mild to moderate nausea). It might be that when watching patterns moving at 7 dps, eye fixation introduced two competing effects: (i) suppression of eye movement reduced levels of VIMS and (ii) increases in peripheral retinal slip velocity increased levels of VIMS. However introducing fixation into stimulated or a VE environment reduces the foveal slip and motion sickness. Retinal image slip promoted by fixational eye movements prevents image fading in central vision. However, in the periphery a higher amount of movement is necessary to prevent this fading. The effects of increased retinal image slip are different for simple (non-crowded) and more complex (crowded) visual tasks. Prior results provide further evidence for the importance of fixation stability on complex visual tasks when using the peripheral retina. This technology can prevent both foveal slip and peripheral retinal slip velocity in a provocative motion environment.

Mismatches can be caused where there are differences in stimuli as processed by the brain. Mismatches can occur where there is motion, or where there is no motion. These mismatches may be caused by delays in the delivery or processing of the stimuli or mismatch of stimuli even without delay. Examples of mismatches are seen in persons suffering from vertigo or persons in a virtual space such as a video game or flight simulator or targeting system. A solution is needed that will enable a person to participate in activities where visual scene motion does not evoke illusory self-motion or motion sickness and participate in motion provocative activities without having motion sickness, spatial disorientation, vertigo and loss of human performance activities.

There is a need for improvements to systems and methods that avoid vertigo, motion sickness, and spatial disorientation integrated in motion sensory provocative environments to avoid problems associated with compromised human performance or even loss of user control. Such an improvement can have application in mitigating, preventing or controlling symptoms of motion sickness, simulation sickness, gaming sickness, spatial disorientation, dizziness, 3-D vision syndrome or vision induced motion sickness in the environments of 3-D or 4-D motion viewing, or viewing any stereoscopic displays such as with operation of remote devices, in simulators, medical imaging, surgical training or operations, virtual environments, scientific visualization, space use, or with gaming devices. An ideal device would be as simple and low cost as possible to broaden its market appeal. It should be able to operate in any kind of lighting environment ranging from broad daylight to nighttime conditions. Ideally, the device would not require any power source.

BRIEF DESCRIPTION OF THE DRAWINGS

The present invention will be better understood on reading the following detailed description of non-limiting embodiments thereof, and on examining the accompanying drawings, in which:

FIG. 21A shows a top view of an embodiment using a mirror, lens, ball and reticle to provide both pitch and roll information off-bore of a user's normal line of sight;

FIG. 21B shows a detail side view of the optical path in the orientation module used by the embodiment shown in FIG. 21A;

FIG. 21C shows a bottom view of the orientation module of FIG. 21B;

Figure 1A:
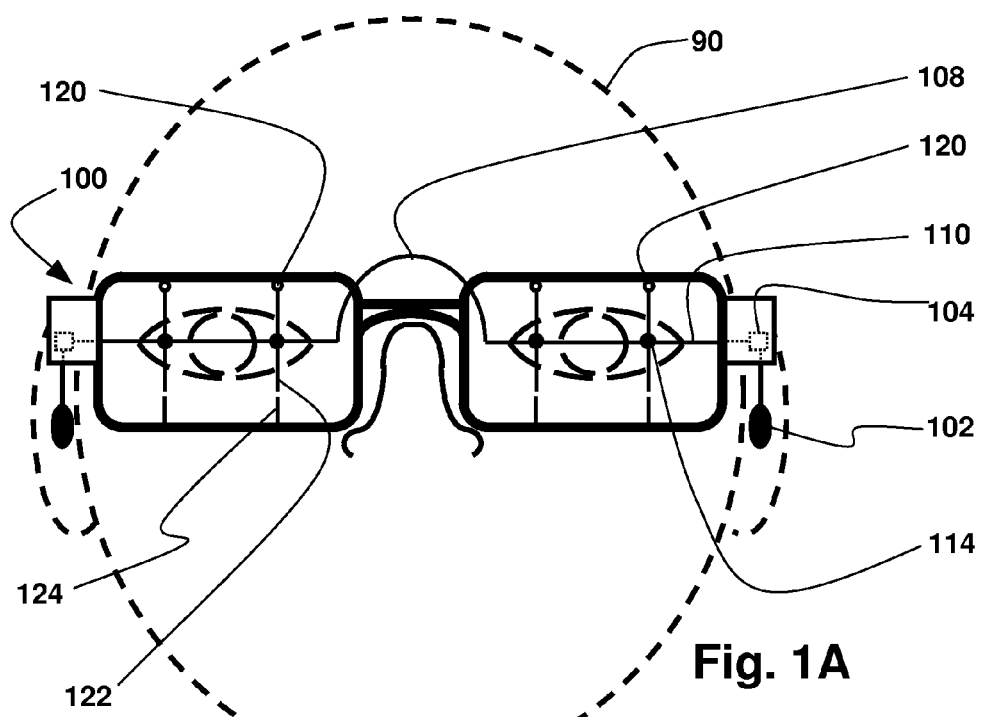
FIG. 1A. is a front view of a pair of eyeglasses having a set of mechanical pendulums that move with pitch and roll of a user's head.

It should be understood that the drawings are not necessarily to scale. In certain instances, details that are not necessary for an understanding of the invention or that render other details difficult to perceive may have been omitted. It should be understood that the invention is not necessarily limited to the particular embodiments illustrated herein.

DETAILED DESCRIPTION

The ensuing description provides preferred exemplary embodiment(s) only, and is not intended to limit the scope, applicability or configuration of the disclosure. Rather, the ensuing description of the preferred exemplary embodiment(s) will provide those skilled in the art with an enabling description for implementing a preferred exemplary embodiment. It should be understood that various changes could be made in the function and arrangement of elements without departing from the spirit and scope as set forth in the appended claims. Specific details are given in the following description to provide a thorough understanding of the embodiments. However, it will be understood by one of ordinary skill in the art that the embodiments may be practiced without these specific details.

Embodiments of the present invention comprise head worn devices and methods for mitigating or preventing motion sickness. Motion sickness can include vertigo, simulation sickness, gaming sickness, spatial disorientation, dizziness, vision induced motion sickness or vection induced motion sickness in 2-D, 3-D, or 4-D environments, including the viewing of displays such as with operation of remote devices, in vehicles, simulators, medical imaging, surgical training or operations, virtual environments, scientific visualization, space use, or entertainment, such as gaming. Some embodiments of the present invention can operate without any electricity, electronics, or active components that consume power. For example, some embodiments of the present invention have no video engine and no battery and use only passive devices with one or two axial orientations to prevent and control motion sickness, motion-induced vision sickness, and other variants of spatial disorientation and vertigo. Embodiments of the present invention can use no electrical signals. Embodiments of the present invention can use purely mechanical devices instead of electro-mechanical sensors or transducers that convert movement to an electrical signal such as accelerometers, gyroscopes, acoustic sensors, magnetic sensors, and optical sensors. Instead, embodiments of the present invention can use purely mechanical devices such as pendulums, rolling elements, and fluids. Embodiments of the present invention can be implemented without using magnets. Embodiments of the present invention can be head worn (for example, helmets, hats, visors, eyewear, or clip on to helmets, face-shields, etc) or eye worn devices with visual displays that provide visual symbology representing a user's position or orientation. By visualizing the information, the sensory mismatch between the sensed labyrinthine signals, the proprioception and visual perception can be controlled or mitigated. Embodiments of the present invention can be used in a variety of environments where motion is present or anticipated or in the presence of provocative visual stimuli. Embodiments of the present invention can be used to control symptoms of sickness associated with motion in simulated environments or 3-D, 4-D, or 5-D elements, atmospheres, settings, situations, conditions, context, mediums, or environments. Embodiments of the present invention can be used to control vertigo for the user who has vertigo, for a person experiencing motion sickness while riding in a vehicle (such as a boat, car, aircraft), or for someone experiencing visually-induced motion sickness from watching a moving image on a stationary screen. Embodiments of the present invention can also be used to mitigate or control spatial disorientation or motion sickness in gaming devices, in a controller or computer format or with simulator use or in a virtual environment or for any simulation sickness. Embodiments of the present invention can also be used in rehabilitation environments for balance stabilization or enhancement.

Generally speaking, embodiments of the present invention sense gravity, micro-gravity, some surrogate for gravity (such as a magnetic force), or inertia (such as centrifugal/centripetal force or Coriolis forces) to move a mechanical element or a fluid in a way that gives a user a visual cue as to his or her orientation with respect to the surrounding environment. The cue can be constant. Such cues override the dysfunctional labyrinth, or stimulated labyrinth and mismatched visual information received and serve to eliminate the sensory mismatch and the resulting sensations of nausea, emesis, blurred vision, or other associated complaints of visual disturbance, headaches, imbalance and loss of human performance activities associated with these variants of motion related or visually related sickness, spatial disorientation or vertigo.

Embodiments of the present invention can include an orientation reference symbol or symbols. For example, there can be a horizontal orientation reference symbol that comprises a line that is fixed relative to the user's head and field of vision, and therefore parallel to the person's interaural axis. This horizontal reference line can then be viewed relative to inertial information that can include an artificial horizon. For purposes of this disclosure, pitch can be defined as rotation of the head about the interaural axis (a line connecting the ears) relative to gravity or relative a fixed reference frame. Synonyms for pitch include azimuth and elevation. For purposes of this disclosure, roll can be defined as rotation of the head about the naso-occipital axis, (a line from the bridge of the nose to the center-point of the line connecting the ears) relative to gravity or relative to a fixed reference frame. The naso-occipital axis (or axis of rotation for roll) can also be thought of as a line perpendicular to the interaural axis that lies in a horizontal plane for a person whose head is in a natural upright position. A fixed horizontal line can be used a pitch orientation reference symbol, it can be used as a roll orientation reference symbol, or it can be used as both a pitch orientation and a roll orientation reference symbol. A vertical line can also be used as an orientation symbol, and can be a pitch orientation reference symbol, a roll orientation reference symbol, or both a pitch orientation and a roll orientation reference symbol. There can be one or more vertical lines. This vertical line or lines can further comprise a vertical scale. There can be separate orientation reference symbols for each eye. A dot can also be used as an orientation reference symbol for pitch, roll, or both pitch and roll. More broadly speaking, any other shape or combination of shapes capable of being understood by anyone skilled in the art can be used as an orientation reference symbol. These orientation reference symbols should be located where they are visible to the user. The orientation reference symbols can be can be in the periphery of the user's vision, either on the side or on the top or bottom. The orientation reference symbols can be in the center of the user's vision. The orientation reference symbols can move from the center to the periphery of the user's vision based on inertial or user input. The orientation reference symbols are fixedly attached or a fixed element of a device that can be fixedly attached to the user's head.

Embodiments of the present invention may include an inertial horizon (sometimes called an artificial horizon) and other visual cues to produce a stable site of visual fixation relative to the user's actual pitch and roll motion. The visual cues may be symbols of any type or shape capable of being understood by anyone skilled in the art. A single visual cue can be used for both pitch and roll or there can be separate (independent) visual cues for pitch and for roll. The visual cues can move in a way that provides a continuously variable (i.e. analog) reading of pitch and roll for a person. There can be separate visual cues for the right eye and the left eye. The visual cues should be located to be visible to the user. The visual cues can be in the periphery of the user's vision, either on the side or on the top or bottom. The visual cues can be in the center of the user's vision. The visual cues can move from the center to the periphery of the user's vision based on inertial or user input. The visual cues are a part of the device that can be fixedly attached to the user's head.

Embodiments of the present invention may be worn on the head and as the user moves, the pitch and roll indicators move respectively. It has been documented with several studies that such feedback controls or mitigates sensory mismatch between the labyrinth/vestibular, visual and proprioceptive systems, so as to give relief to those people who experience motion sickness, spatial disorientation or suffer vertigo and can help to provide visual feedback to those people undergoing rehabilitation for balance stabilization, control or enhancement. In particular, it is possible to provide visual feedback that matches the vestibular pitch and roll information for a healthy normal person. This satisfies a long existing need for a mechanical system capable of controlling the sensory mismatch, which is induced by environmental conditions or labyrinthine/vestibular system dysfunction, or stimulation, visual disturbance or provocative stimulation or dysfunction of proprioceptive response or stimulation. It can be presented in a monocular or binocular fashion and it is inexpensive and can eliminate the need for a video engine, a power supply, and electronics of any kind. It should be noted that many embodiments of the present invention do not include any reference information for yaw (i.e. rotation about an vertical axis for a person standing upright), the primary axes of rotation for embodiments of the present invention are pitch and roll.

Embodiments of the present invention may be implemented in ways that makes the cues visible in bright light or in darkness. The visual cues can be located so they do not interfere with vision (e.g. the user can continue to see through the display to see other objects or perform other tasks—it is available to the user upon need). One analogy is that of looking at a baseball game through a wire fence in that after moments of focusing on the play action the fence is not noticed, but upon need the fence can be focused upon.

Embodiments of the present invention may include symbology. Of critical importance to success of the system is the symbology of the cues provided to the user to prevent, avoid, and ameliorate motion sickness, spatial disorientation or vertigo. Not only is the information provided important but also experience demonstrates that the way in which information is presented is critical to successful use of the system. The following describe embodiments of symbology that has been demonstrated to be successful. Many factors are important to the success of the cue symbology such as, shape(s), color(s) and dynamic mechanization(s) of the symbology as used in various embodiments for various applications.

The artificial horizon or inertial horizon provides the user with a stable position on which to focus when experiencing symptoms of motion. If vertigo is present the user can focus on this stable line or can more specifically focus on a point on this line, such as a center point or an off-bore point, with the fovea of the eye. When focusing on this point, the effects of pitch and roll motion are decreased and the user can then have increased cognitive task performance as a result of lessening the visual-vestibular conflict.

Embodiments of the present invention may include a roll indicator that can enhance proprioception by visual confirmation of head and body location and movement. The combination of an inertial horizon and a roll indicator also confirms what the inner ear and the proprioception have sensed when there is no or limited visual reference, such as in darkness, or when the visual information is misleading. In the absence of vision, the head is not able to maintain a stable position. Labyrinth-defective subjects use proprioceptive cues to perceive body position. In vibration or provocative motion environments the proprioceptive system is decrease. The particular combinations of symbology and symbology elements and functions may vary. The variety may in whole or in part be driven by the application in which the embodiment is intended for use.

Embodiments of the present invention may include either an Offset or a Bore Sight Display. The location of the symbology may be offset from the center bore sight to allow the user to better see through the display and to enhance compatibility with other optical displays such as head-mounted displays or night vision equipment and symbology such as fire control targeting symbology. In one embodiment the symbology is presented off bore sight to one side or the other (preferably to the left for the left eye or to the right for the right eye. When the symbology is displayed off bore sight, it may be shrunk to fit. In some embodiments, the symbology can still however be set on bore-sight taking the same view-space of his other instruments if desired by the user.

Embodiments of the present invention may include a monocular or binocular display. The display can be presented to the user either as a monocular or binocular see-through display and can be eye worn, head worn or mounted to a helmet or head worn device.

Embodiments of the present invention may be adaptable to various carriers. For example embodiments of the present invention can be detachably attached to hats, glasses, a helmet, a head-mounted display, binoculars, goggles, scuba masks, face shields, and any other user worn device. Embodiments of the present invention could also be integrated into any head-mounted devices such as the ones mentioned in the previous sentence. Embodiments of the present invention can be directly attached to the head, independent of any other head-worn devices. Embodiments of the present invention are typically implemented in the user's viewing region and within several inches of the eyes. For that reason, these embodiments typically will include a clear lens or see-through window or shield and these lenses, windows, or shields will typically have a non-opaque region through which the user can see directly ahead. These lenses, windows, or shields could be made out of glass or a plastic (i.e. polymer) such as polycarbonate, acrylic, or polystyrene, or some blend of multiple polymers. The fabrication of these lenses, windows or shields is something capable of being understood by anyone skilled in the art.

Figure 1B:
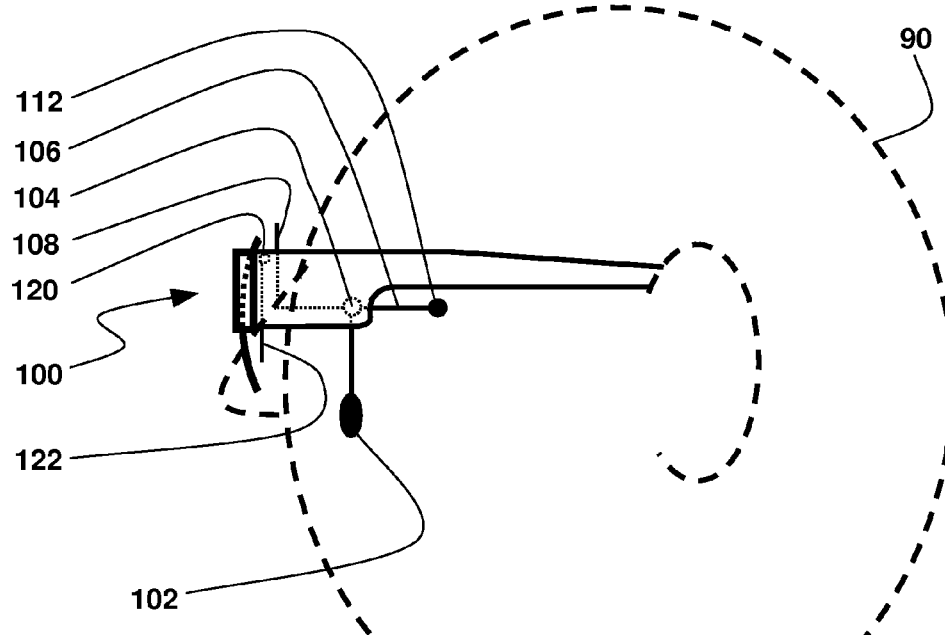
FIG. 1B is a side view of the eyeglasses of FIG. 1A.

Referring now to the figures, FIGS. 1A and 1B show an embodiment of the present invention that relies exclusively on pendulums. This embodiment is in the form of pitch/roll eyeglasses, shown at 100. These eyeglasses have been placed on a user's head, shown at 90. The pitch/roll eyeglasses 100 are comprised of a pitch pendulum shown at 102. In the embodiment shown, there are pitch pendulums 102 on the legs on both sides of the eyeglass frame. The pitch pendulums 102 rotate about an interaural axis at a pitch pendulum pivot point, shown at 120. The pitch pendulums 102 are coupled to pitch linkages, one of which is shown at 106, and the other of which is on the right leg of the glasses. One end of each pitch linkage 106 connects to an inertial pitch horizon bar, shown at 110. In the embodiment shown, there is an inertial pitch horizon bar 110 for each eye and the two inertial pitch horizon bars 110 are connected to each other through an inertial pitch horizon linkage 108 that has been shaped to clear the nose for most head orientations. The other side of each pitch linkage 106 is connected to a pitch counterweight, shown at 112. The pitch counterweights 112 ensure that the pitch assembly, comprising items 102, 104, 106, 108, 110, and 112 hangs correctly when the user has their head in a level position. The eyeglasses 100 can also have one or more primary head rotation reference symbols, shown at 114. In this case, the primary head rotation reference symbols 114 are circular dots and there are four of them, two for each eye. Using circular dots for head rotation reference symbols have experimentally been found to be useful because they give the user some fixed points to focus on (i.e. eye fixation elements), which can minimize distractions from other things going on in the environment, reduce eye twitching (i.e. nystagmus), and reduce physiological motion sickness, spatial disorientation, etc. The primary head rotation reference symbols 114 are designed to move with the head and the glasses. In this embodiment the primary head rotation reference symbols 114 are attached or printed to the lenses of the glasses. The primary head rotation reference symbols 114 in this embodiment will appear above or below the inertial pitch horizon bar 110 when the user's head is pitched forward or backward, providing a visual signal to the user that his/her head is pitched forward or backward. It should also be noted that the pitch pendulum pivot points 120 in this embodiment are located to align with the pitch axes of the eyes so that the inertial pitch horizon bar 110 moves up and down a distance that matches where the user's visual system would expect a true horizon to be if a person tilted his/her head forward or backward in a gravitational environment that was free of other inertial influences (such a centrifugal or Coriolis forces).

The pitch/roll eyeglasses also have roll pendulums, shown at 122. The embodiment shown has four roll pendulums 122, two for each eye. The roll pendulums in this embodiment are attached to the glasses above the lenses through roll pendulum pivot points, shown at 120. The roll pendulum pivot points 120 allow each roll pendulum 122 to rotate when the user's head is rolled about naso-occipital axis. In addition to the primary head rotation reference symbols 114, there are additional roll reference symbols, shown at 124 that give further indication to the amount of roll of the person's head. In the embodiment show, the roll reference symbols 124 are in the form of vertical lines that align with the vertical lines of the roll pendulums 122 when the person's head is in a neutral (neither pitched nor rolled) position.

Figure 2A:
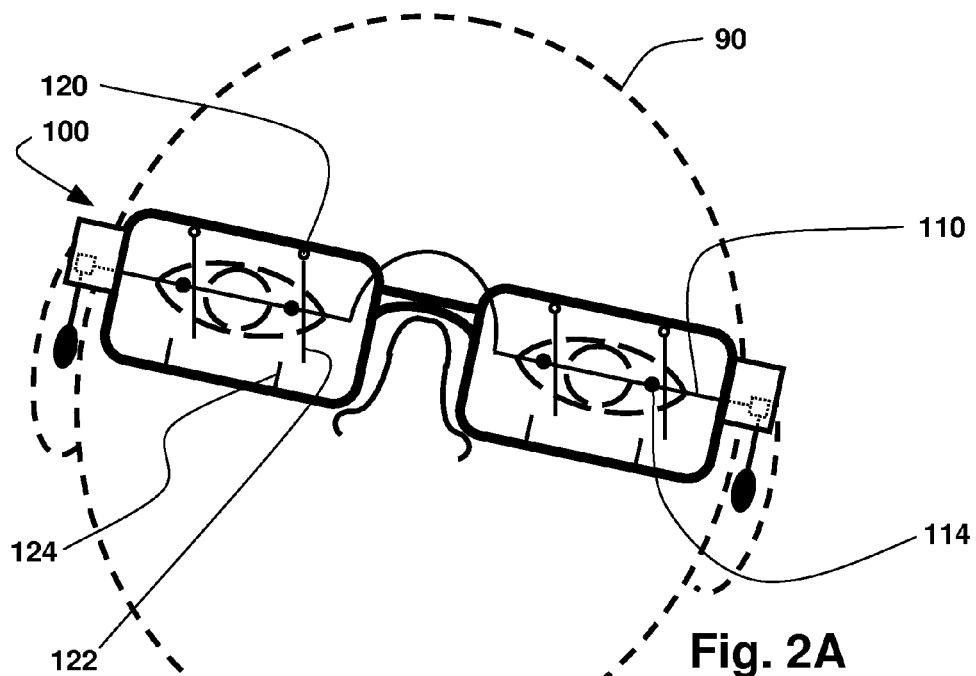
FIG. 2A is a front view of the eyeglasses of FIG. 1A when the user's head is rolled to down to the user's left.

FIG. 2A shows how the visual cues for the embodiment of the pitch/roll eyeglasses 100 shown in FIG. 1A and FIG. 1B change when the user's head 90 is rotated (rolled) down to the left. In this case the inertial pitch horizon bar 110 does not move relative to the user's head when the user's head is rolled in the absence of any change in pitch. The roll pendulums 122, rotate about the roll pendulum pivot points 120 in order to continue to align with gravity about the naso-occipital axis. This creates an offset between the roll pendulums 122, and the primary head rotation symbols reference symbols 114 as well as between the roll pendulums 122 and the roll reference symbols 124.

Figure 2B:
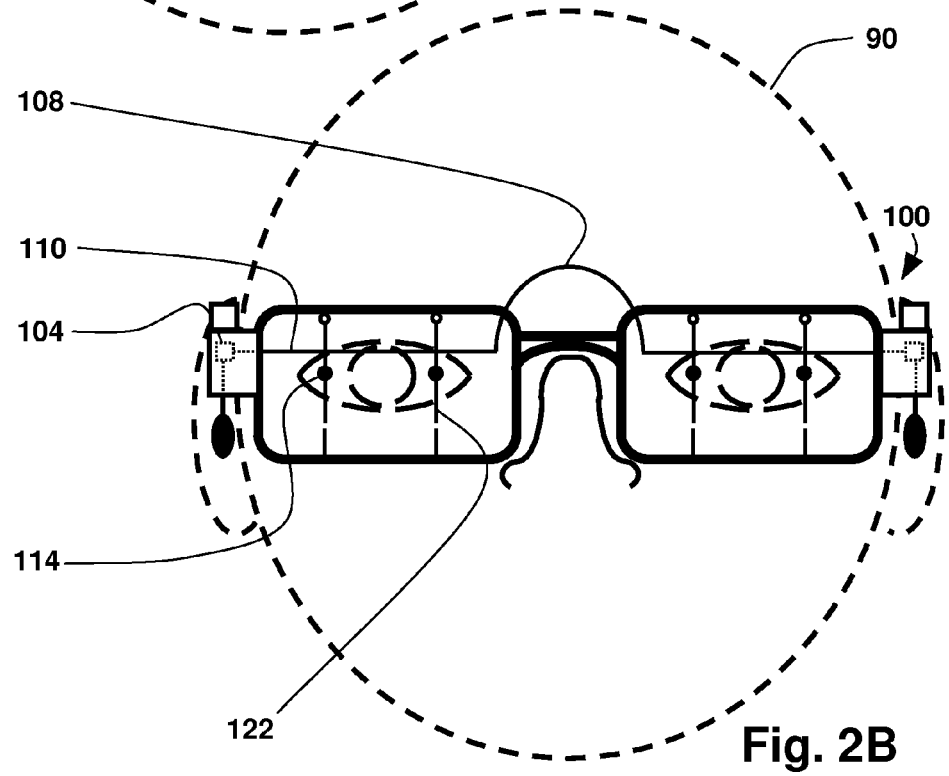
FIG. 2B is a front view of the eyeglasses of FIG. 1A when the user's head is pitched forward.

FIG. 2B shows how the visual cues for the embodiment of the pitch/roll eyeglasses 100 shown in FIG. 1A and FIG. 1B change when the user's head 90 is rotated (pitched) forward. In this case the inertial pitch horizon bar 110 moves upward in the user's field of view, creating an offset between the primary head rotation reference symbols 114 and the inertial pitch horizon bar 110. The inertial pitch horizon bars rotate about the pitch pendulum pivot points 104. The inertial pitch horizon linkage 108 (attaches the inertial pitch horizon bars 110 for each eye to each other) also moves up the same distance. In this embodiment, the roll pendulums, 122 do not move when the head is pitched, but not rolled.

Figure 3A:
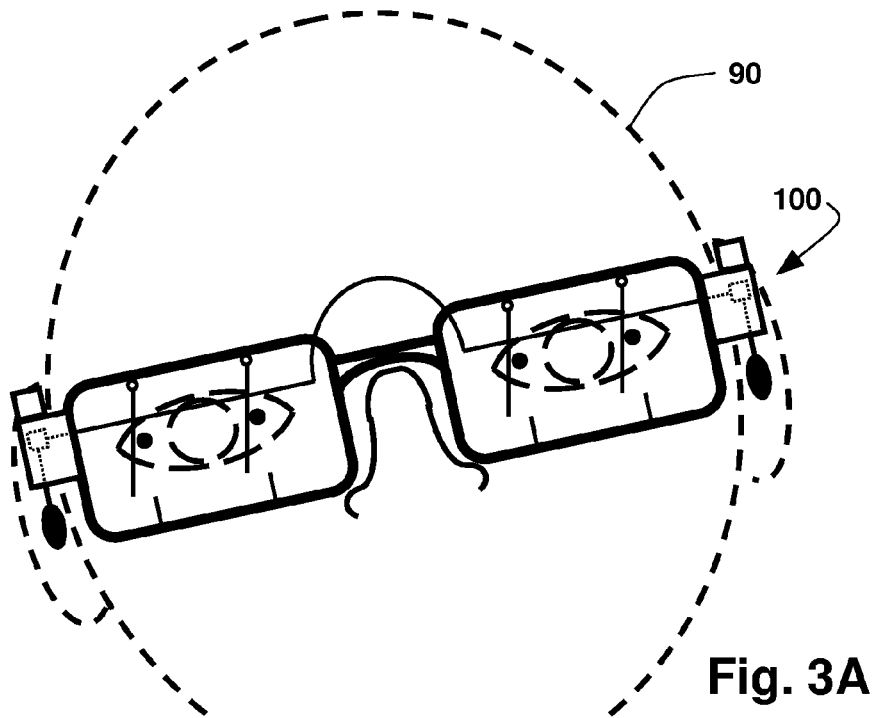
FIG. 3A is a front view of the eyeglasses of FIG. 1A when the user's head is rolled to the user's right and the user's head is pitched forward.
Figure 3B:
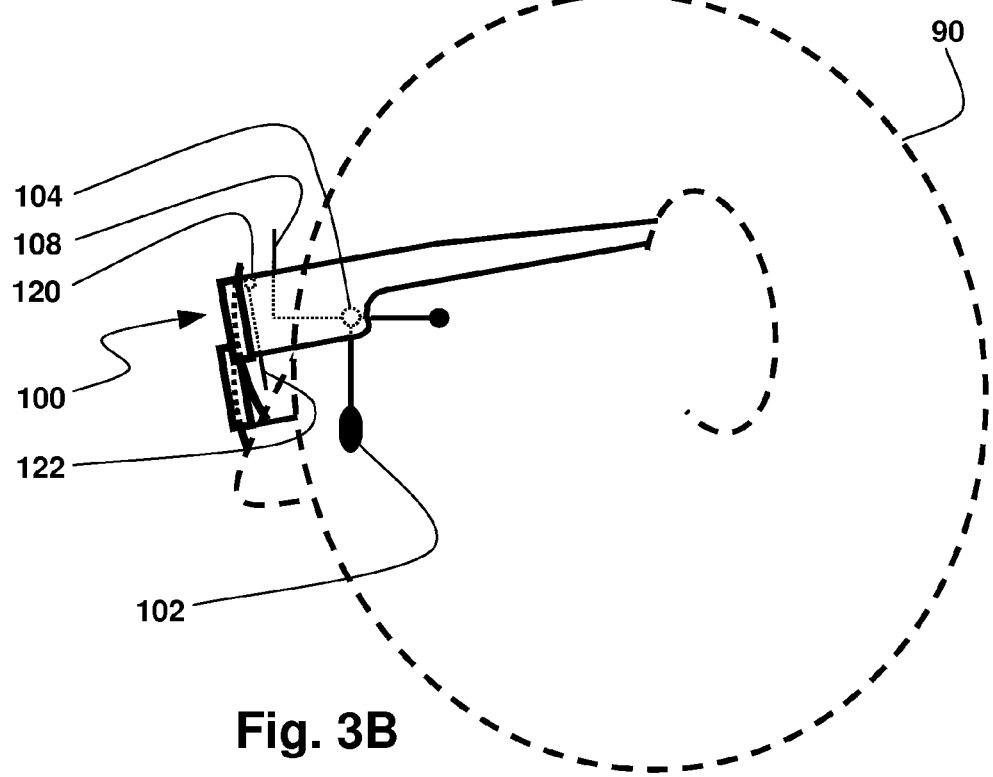
FIG. 3B is a side view of the eyeglasses of FIG. 1A when the user's head is rolled to the user's right and the user's head is pitched forward.

FIG. 3A and FIG. 3B show a front and side view, respectively, of the embodiment of the pitch/roll eyeglasses 100 shown in FIG. 1A and FIG. 1B when the head 90 is both rolled to the left and pitched forward. As shown in FIG. 3A, both the inertial pitch horizon bar 110 and the roll pendulums 122 move relative to the primary head rotation reference symbol 114 when the head is both pitched and rolled. The side view shown in FIG. 3B illustrates how the pitch pendulum 102 continues to hang vertically below the pitch pendulum pivot point 104 and how this causes the inertial pitch horizon linkage 108 (as well as the inertial pitch horizon bars 110, which are difficult to see in this view) to move upward relative to the eyeglass lenses. The roll pendulum pivot points 120 move with the eyeglass lenses as the head is pitched forward and backward about the interaural axis. When looked at from a side view, the roll pendulums 122 appear not to move.

Figure 4A:
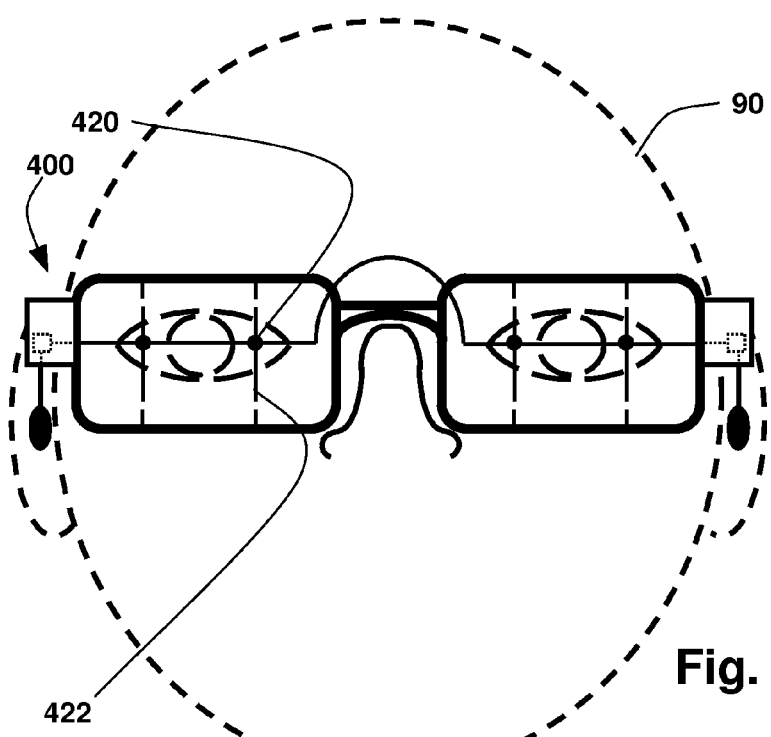
FIG. 4A is an alternate embodiment of a pair of eyeglasses having a set of mechanical pendulums that move with pitch and roll of a user's head.
Figure 4B:
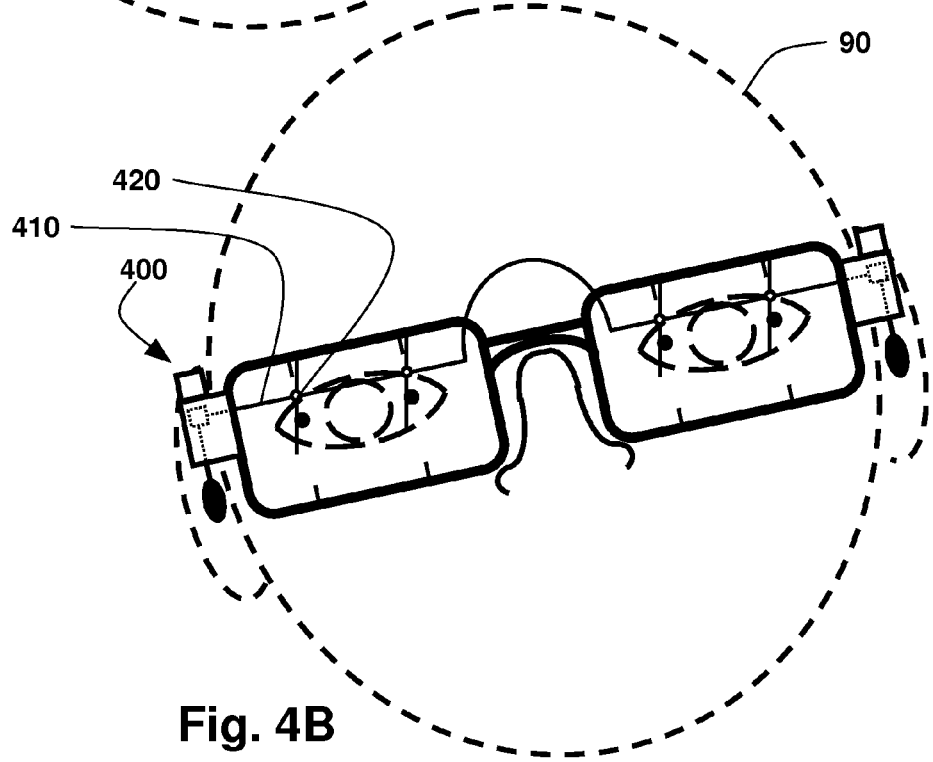
FIG. 4B is a front view of the eyeglasses of FIG. 4A when the user's head is pitched forward and rolled to the user's right.

Further referring to the figures, FIGS. 4A and 4B show an alternate pitch/roll pendulum eyeglass embodiment at 400 mounted on a user's head 90. The alternate eyeglasses 400 have alternate roll pendulums 422 hanging from alternate roll pendulum pivot points 420 attached to alternate inertial pitch horizon bars 410. In this alternate configuration, the alternate pendulums 422 move up and down as the user's head 90 is pitched forward or backward as well as rolling when the user's head rolls.

Figure 5A:
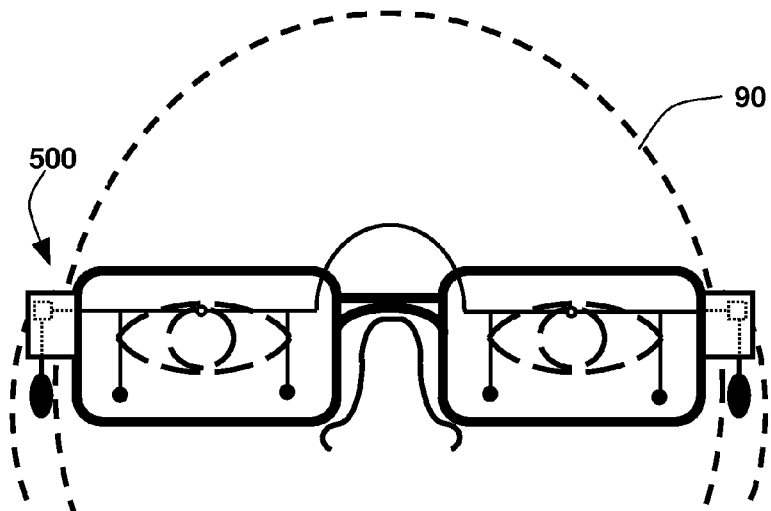
FIG. 5A is another embodiment of a pair of eyeglasses having a set of mechanical pendulums that move with pitch and roll of a user's head.
Figure 5B:
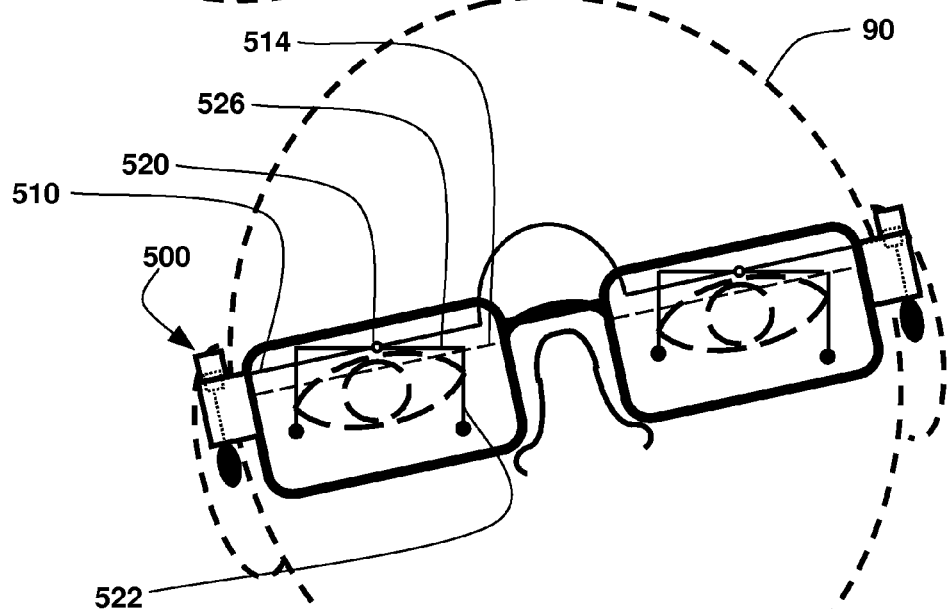
FIG. 5B is a front view of the eyeglasses of FIG. 5A when the user's head is pitched forward and rolled to the user's right.

FIGS. 5A and 5B show another pitch/roll pendulum eyeglass embodiment at 500 mounted on a user's head 90. These other eyeglasses 500 have other another roll pendulum 522 hanging from another pivot pendulum point 520 that is attached to another horizontal bar 510. This other eyeglass embodiment 500 also has horizontal roll pendulum linkages 526 and uses a horizontal line positioned on each lens as another primary head rotation reference symbol 514.

Figure 6A:
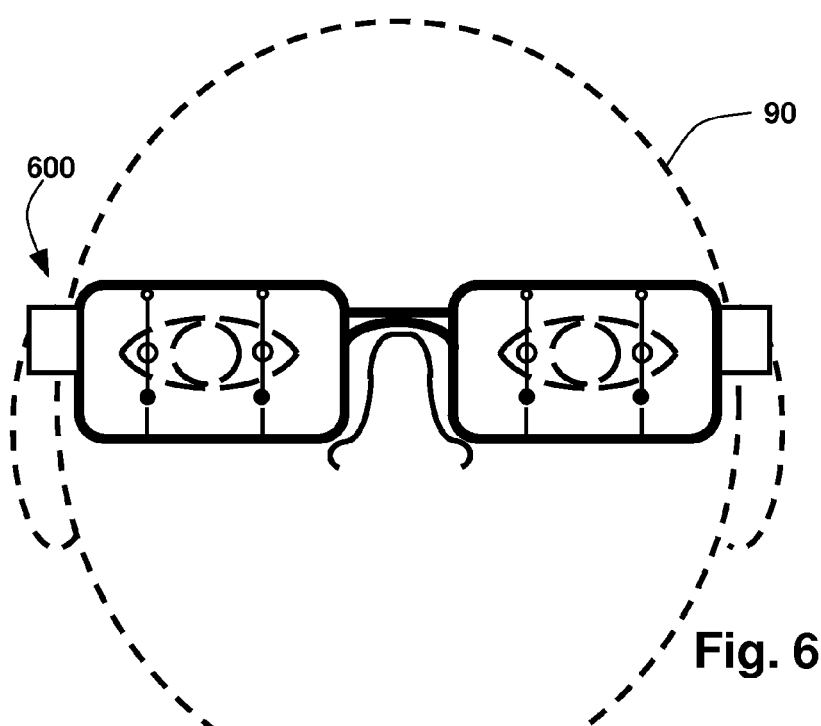
FIG. 6A is an embodiment of a pair of eyeglasses having a set of mechanical pendulums for roll without having a mechanism for detecting or presenting pitch information.
Figure 6B:
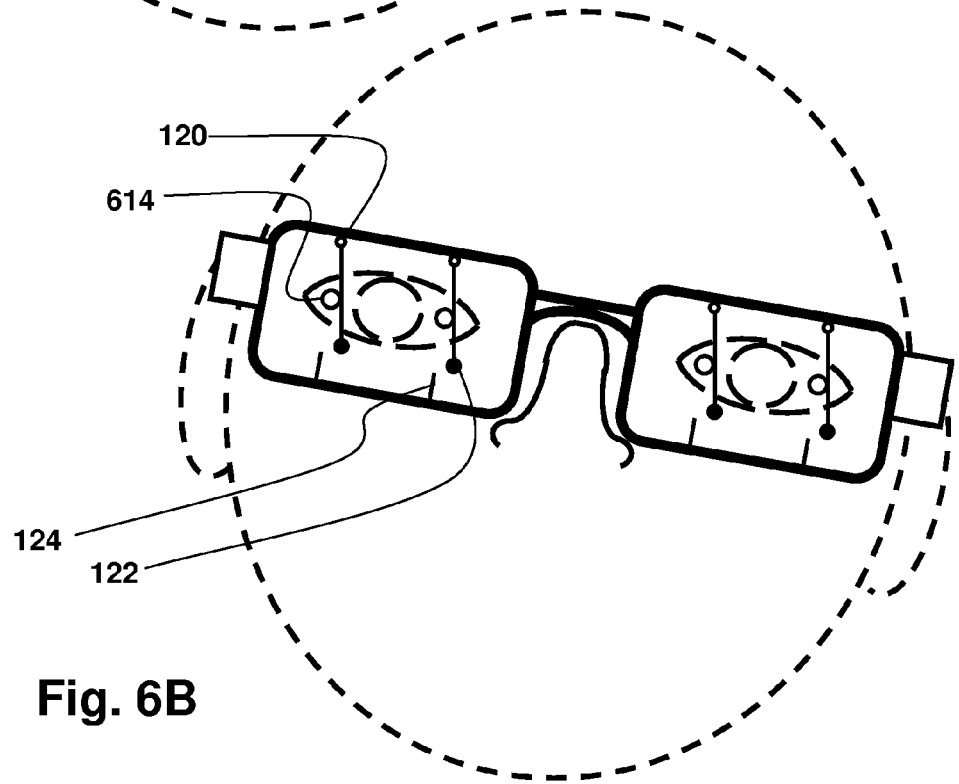
FIG. 6B is a front view of the eyeglasses of FIG. 6A when the user's head is pitched forward and rolled to the user's left.

FIGS. 6A and 6B show roll-only pendulum eyeglasses 600 mounted on a user's head 90. These roll-only pendulum glasses 600 have four roll-only pendulums 122 that are connected through four roll pendulum pivot points 120 to the frame of the eyeglasses in a manner similar to that shown in FIG. 1A. These roll-only pendulum glasses 600 also have roll reference symbols 124 that are similar to those of FIG. 1A. The embodiment shown in FIGS. 6A and 6B uses an alternate embodiment of a primary head rotation reference symbol 614 in the form of an open circle that moves with the lenses of the glasses. Note that the pendulums shown in FIG. 6B can also be called plumb bobs. It is also worth pointing out that these pendulum or plumb bobs could also be immersed in a liquid by, for example, combining elements of the embodiment shown in FIG. 6A and FIG. 6B with elements of the fluid-filled embodiments shown in FIGS. 14A-17B.

Figure 7A:
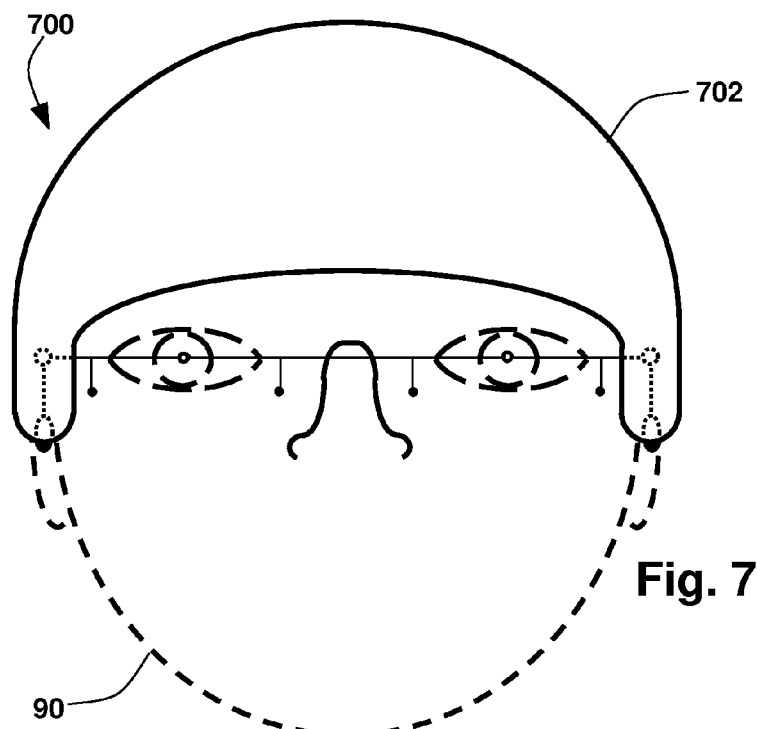
FIG. 7A is a front view of a pitch and roll indicating pendulum device integrated into a helmet.
Figure 7B:
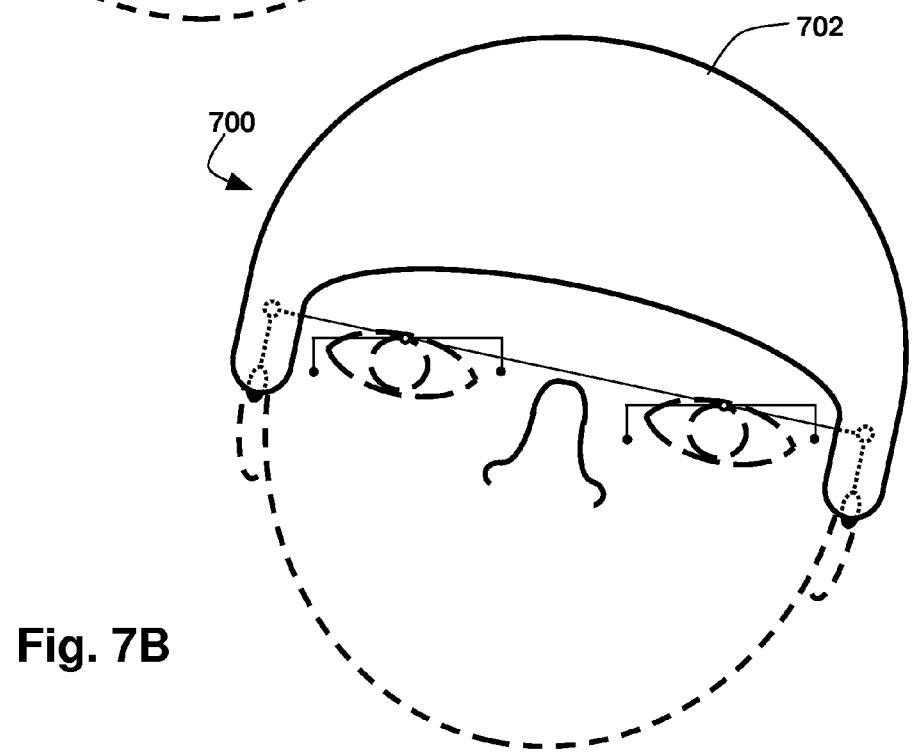
FIG. 7B is a front view of the device of FIG. 7A with the user's head pitched forward and rolled down to the user's left.

FIGS. 7A and 7B show an embodiment of the present invention in the form of a pitch/roll pendulum helmet at 700 mounted on a user's head 90. In this embodiment, an arrangement similar to the one shown in FIG. 5A and FIG. 5B has been mounted onto a helmet 702. The FIG. 7A shows a front view of this embodiment 700 in a neutral (no pitch and no roll) configuration. FIG. 7B shows this embodiment 700 in a configuration where the user's head is pitched forward and rolled to the left.

Figure 8A:
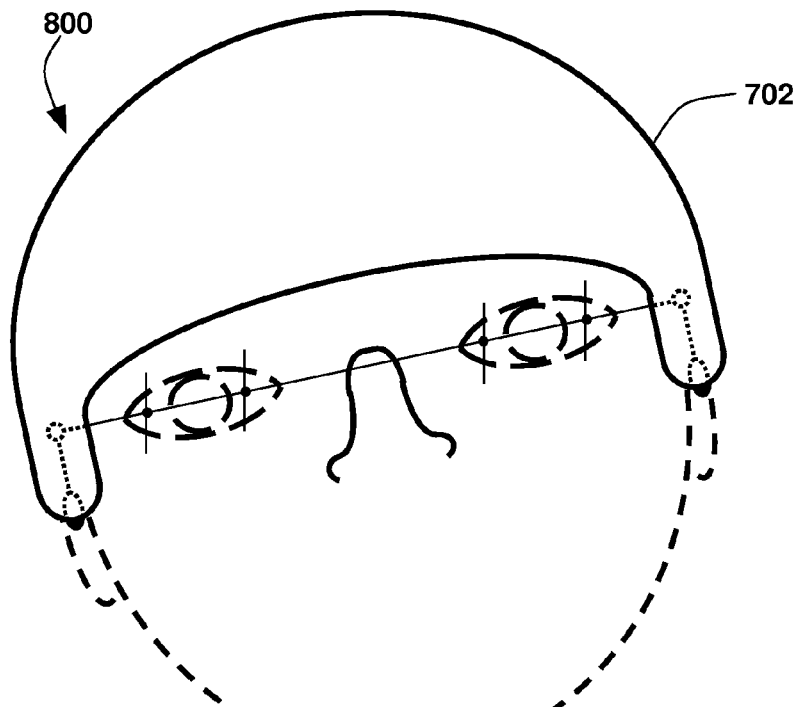
FIG. 8A is a front view of an alternate embodiment of a pitch and roll indicating pendulum device integrated into a helmet.

FIG. 8A shows an embodiment of a pitch-roll pendulum helmet at 800 that incorporates the features of the alternate pitch/roll eyeglasses that were shown in FIG. 4A and FIG. 4B. This illustrates that is possible to incorporate many of the same features of the embodiments for eyeglasses into embodiments for helmets. It should further be noted that there are many more head worn articles that can incorporate the mechanical pitch and roll systems described here including visors, face shields, baseball caps, and any other head-worn item capable of being understood by anyone skilled in the art.

Figure 8B:
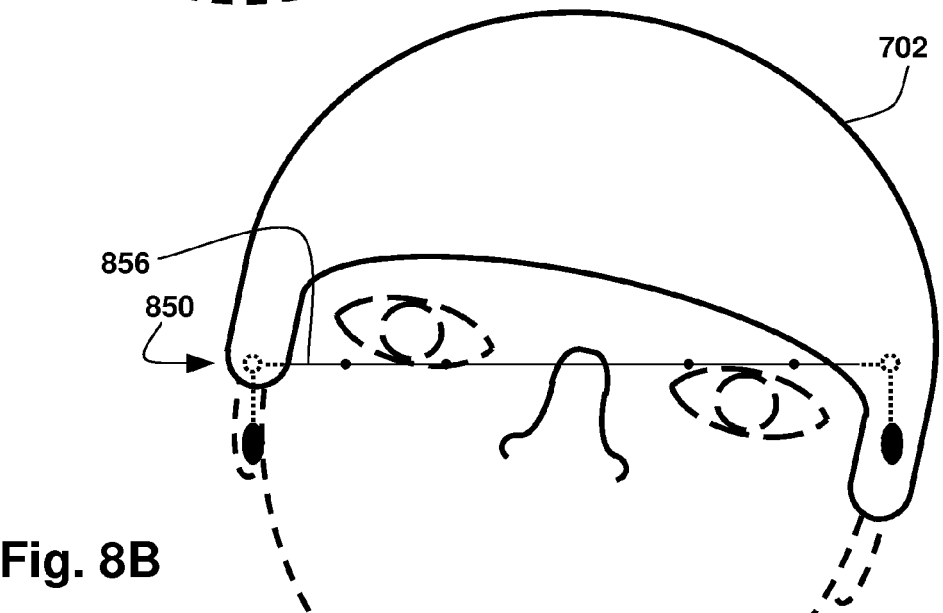
FIG. 8B is a front view of another embodiment of a pendulum device integrated into a helmet that only provides roll feedback.

FIG. 8B shows an embodiment of a single primary head rotation reference symbol helmet 850 that provides pitch and roll information in the form of a single unit inertial pitch horizon bar 856 that pitches and rolls as a single unit across both eyes. This configuration 850 can be implemented through the use of a pendulum and a pivot aligned with the naso-occipital axis at the back of the head or through the use of rolling elements in the helmet linked to rotate the single unit inertial pitch and roll linkage 856 about the naso-occipital axis that are coupled to a pendulum hanging below the chin.

Figure 9A:
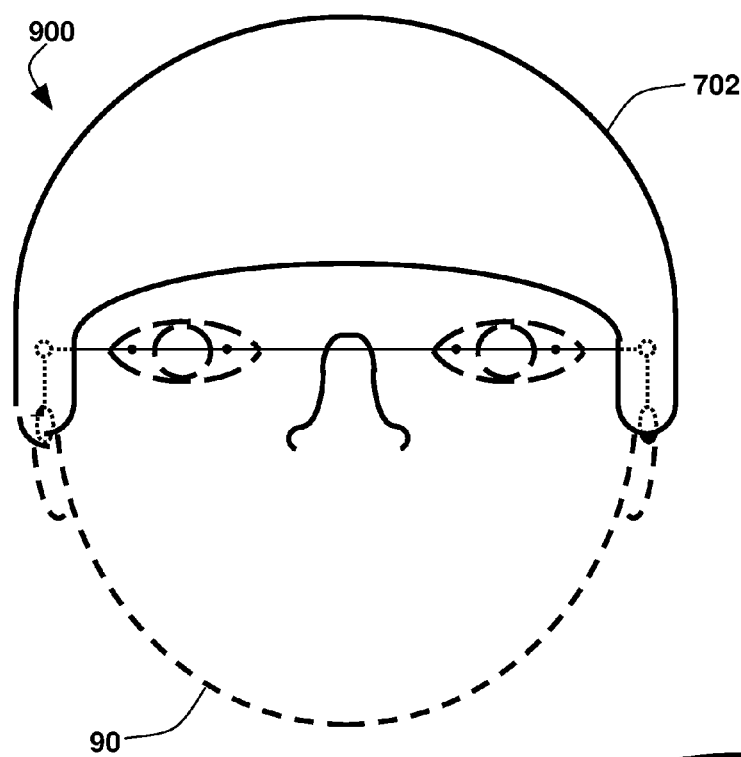
FIG. 9A is a front view of a pendulum-based device integrated into a helmet that only provides pitch visual feedback to the user.
Figure 9B:
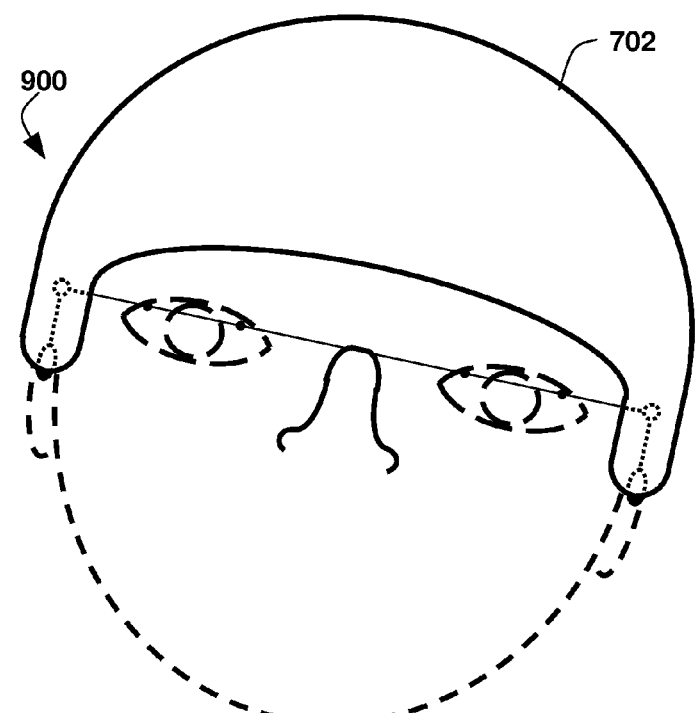
FIG. 9B is a front view of the device of FIG. 9A with the user's head pitched forward and rolled down to the user's left.

FIGS. 9A and 9B show an embodiment of a pitch-only helmet at 900. This pitch-only helmet 900 is similar to other embodiments shown in previous figures, but does not have any mechanism or symbology to display roll. This can be seen by comparing the pitch only helmet 900 on a user's head 90 that is in a neutral position (no pitch and no roll) in FIG. 9A, with the same pitch only helmet 900 on the user's head 90 when the head 90 is pitched forward and rolled left.

Figure 10A:
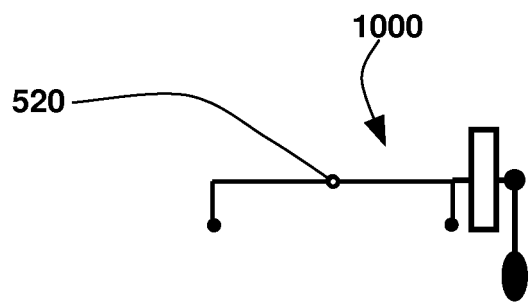
FIG. 10A is a front view of a pendulum device that can be clipped onto another head-worn device such as a helmet or glasses.
Figure 10B:
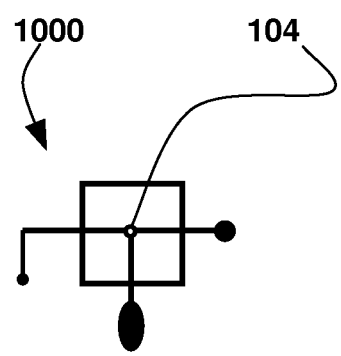
FIG. 10B is a side view of the clip-on device of FIG. 10A.

FIGS. 10A and 10B show another embodiment of the present invention in the form of a pitch/roll pendulum clip-on at 1000. The clip-on 1000 functions similarly to the alternate pitch/roll eyeglasses embodiment shown in FIG. 5A and FIG. 5B, without the eyeglasses. FIG. 10A shows a view of the clip-on 1000 in an orientation equivalent to looking at a user's face from the front and FIG. 10B shows the same clip-on from the side. The clip-on has the same pitch pendulum pivot point 104 that was shown and described with reference to FIG. 1A, and the same other roll pendulum point 520 that was shown and described with reference to FIG. 5A. The clip-on 1000 can be designed to attach to eyeglasses, helmets, face shields, a person's ears, baseball caps, visors, headbands, or any other device capable of being understood by anyone skilled in the art.

Figure 11A:
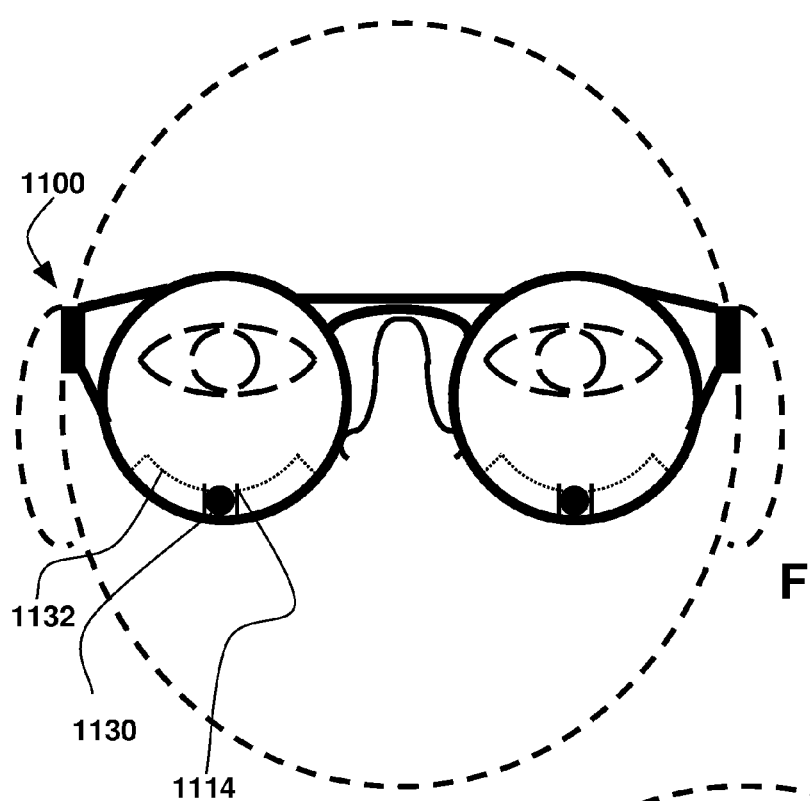
FIG. 11A. is a front view of a pair of eyeglasses having two rolling elements that move with roll of a user's head.
Figure 11B:
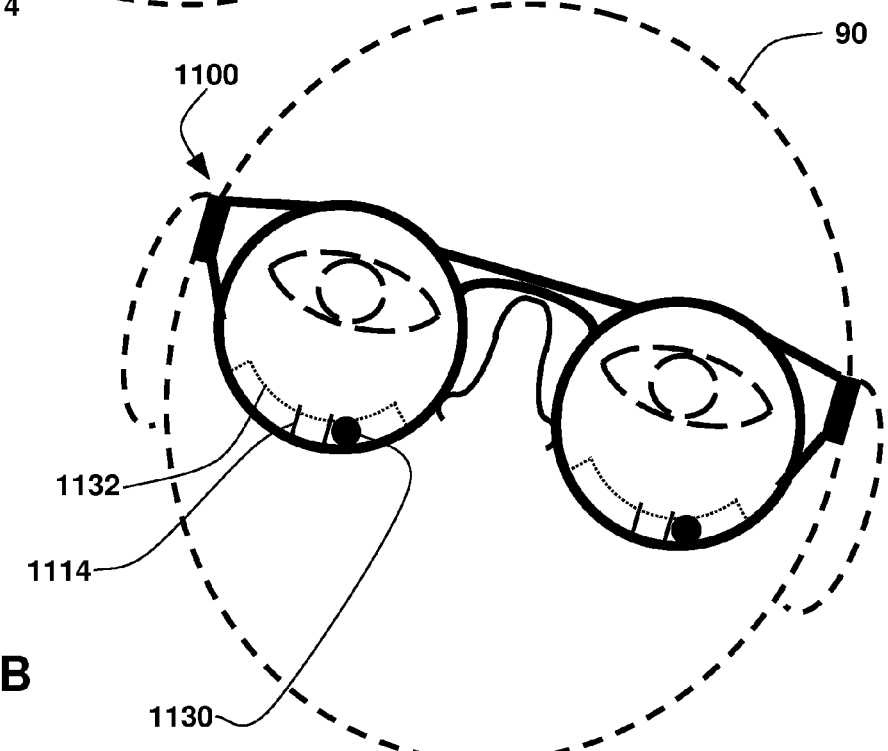
FIG. 11B is a front view of the eyeglasses of FIG. 11A when the user's head is rolled down to the user's left.

FIGS. 11A and 11B show an embodiment of the present invention in the form of roller eyeglasses at 1100. The roller eyeglasses use a rolling element 1130 that is retained in a track 1132 to keep the rolling element 1130 adjacent to one or both of the lenses in a pair of eyeglasses. The roller eyeglasses 1100 can also incorporate indicator line primary head rotation reference symbols, shown at 1114. FIG. 11B shows that rolling of the user's head 90 (to the left in this case) will result in the rolling elements 1130 moving relative to the indicator line primary head rotation reference symbols 1114, providing the user with visual feedback of inertial head rotation in the roll direction. The rolling elements 1130 can be of any shape that rolls and is capable of being understood by anyone skilled in the art. Examples include spheres (or balls), cylinders, cones, any other shape that is rotationally symmetric about an axis of rotation.

Figure 12A:
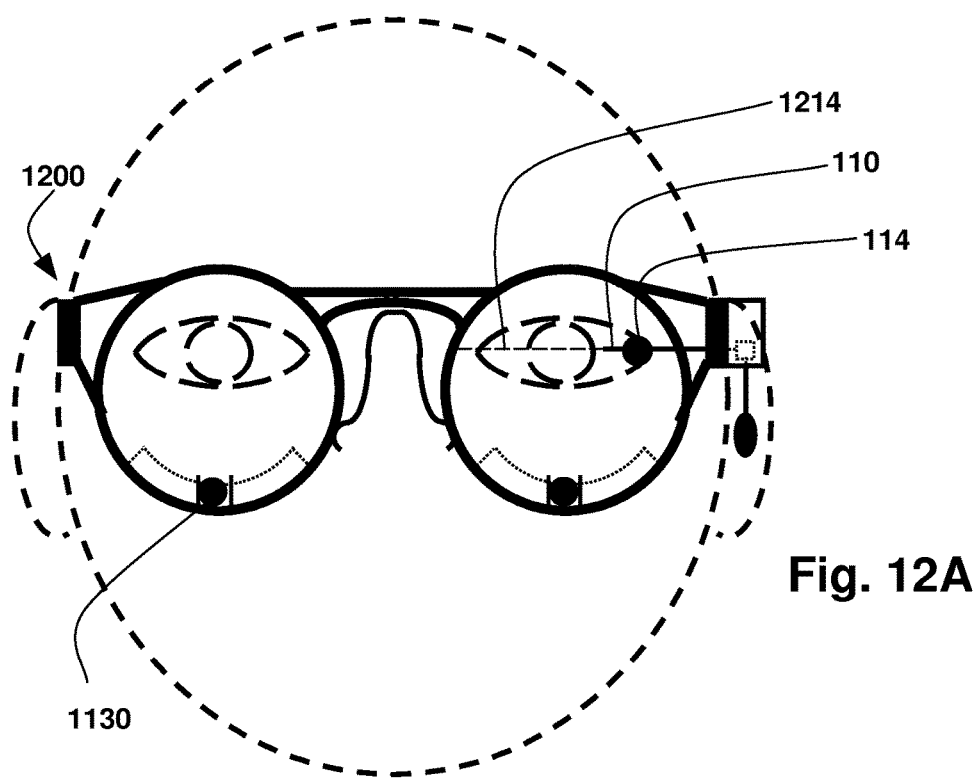
FIG. 12A. is a front view of the glasses of FIG. 11A that also include a pendulum mechanism and artificial horizon in the left lens to provide pitch information.
Figure 12B:
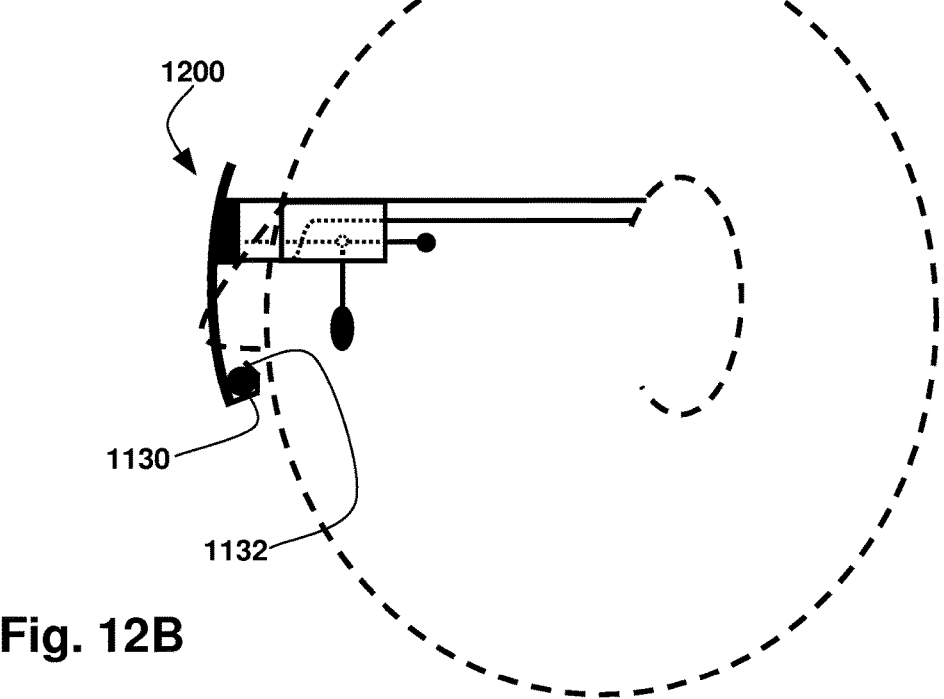
FIG. 12B is a side view of the eyeglasses of FIG. 12A.
Figure 13A:
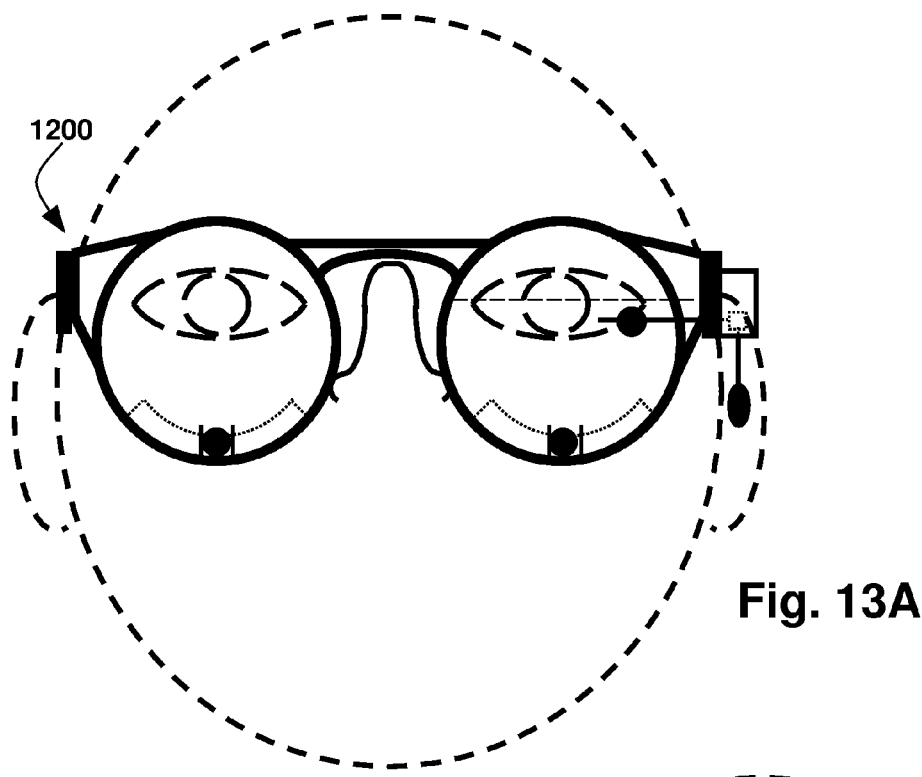
FIG. 13A is a front view of the glasses of FIG. 12A with the user's head pitched backwards.
Figure 13B:
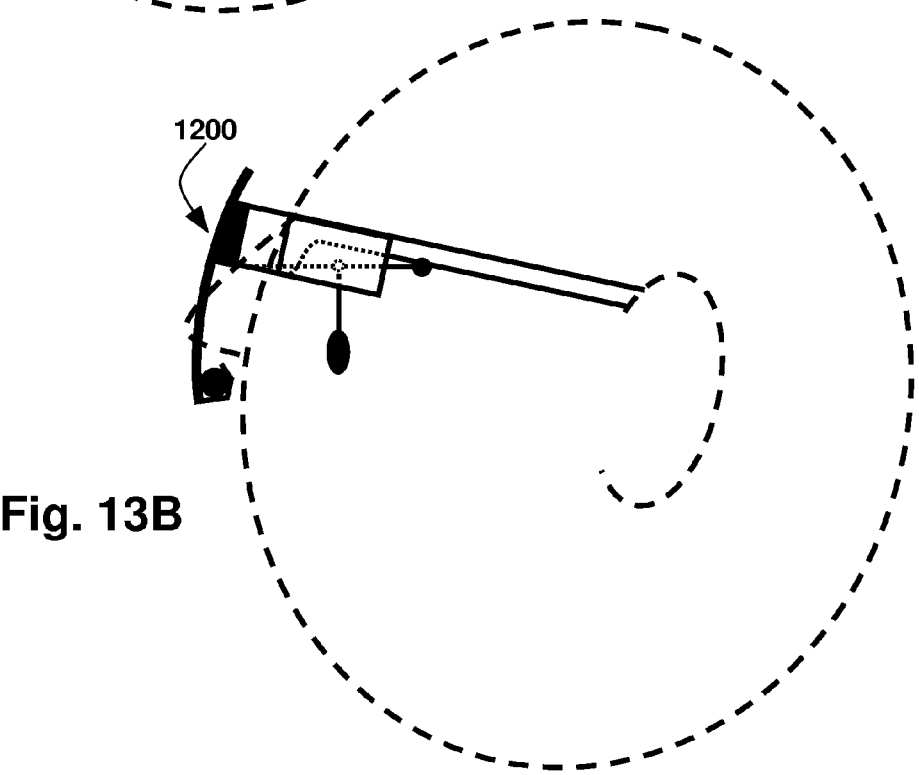
FIG. 13B is a side view of the glasses of FIG. 13A with the user's head pitched backwards.
Figure 14A:
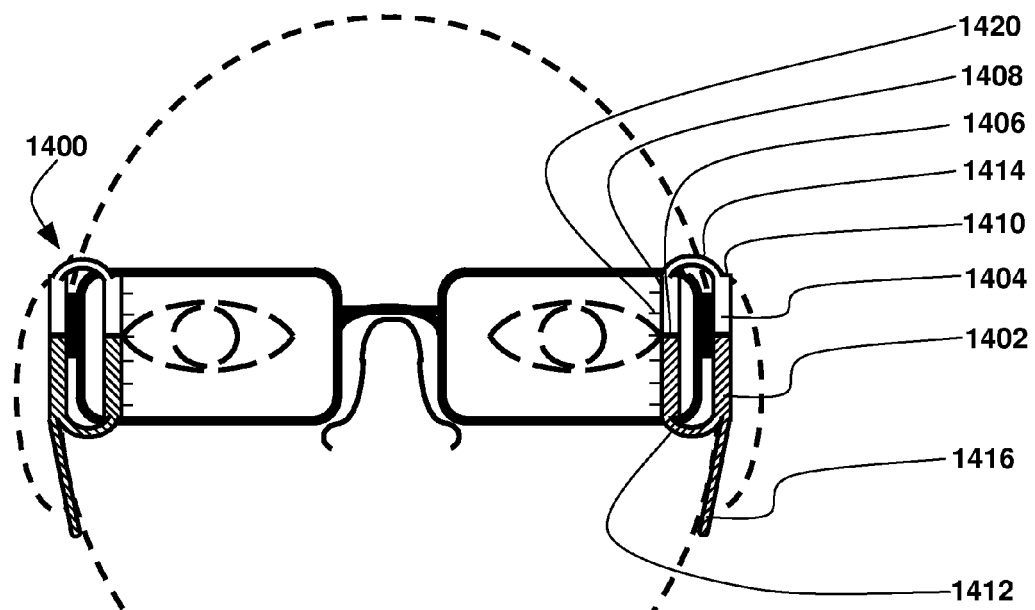
FIG. 14A. is a front view of a pair of eyeglasses having a fluid level that moves with pitch and roll of a user's head.
Figure 14B:
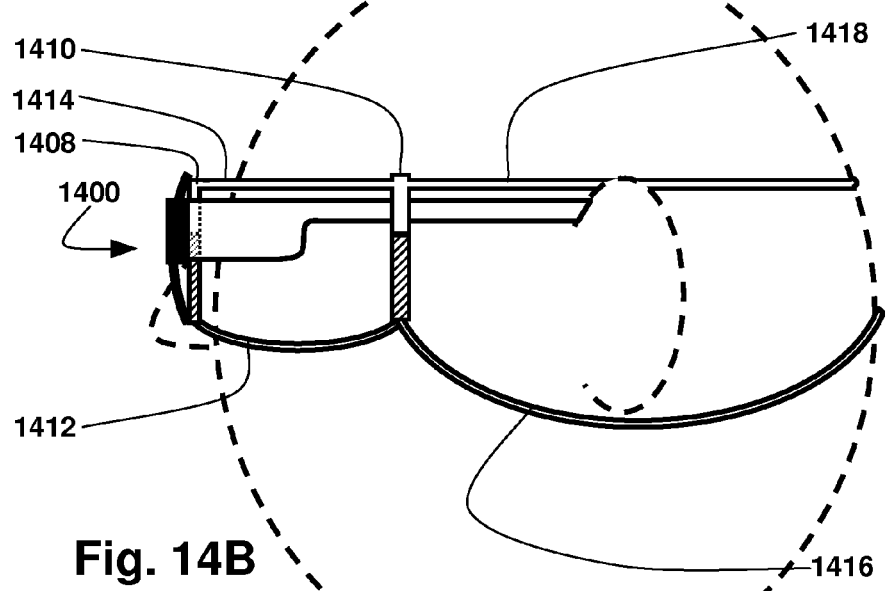
FIG. 14B is a side view of the eyeglasses of FIG. 14A.

FIG. 12A and FIG. 12B illustrate a compound mechanical pitch/roll eyeglasses 1200 that combine the rolling elements 1130 of FIG. 11A and FIG. 11B with a pitch indicator inertial pitch horizon bar 110 (and related pendulum-based actuation elements) of FIG. 1 as well as the primary head rotation reference symbol 114 for one eye that is similar to that of FIG. 1. A secondary head rotation reference symbol 1214 in the form of an etched line in the lens of the glasses is also illustrated in the embodiment of FIG. 12A. FIG. 12B provides a side view of the embodiment of FIG. 12A and this side view also shows the track 1132 that retains the rolling element 1130, which was also discussed, but not shown, with reference to FIG. 11A and FIG. 11B. FIG. 13A and FIG. 13B shows a front view and a side view, respectively, of the compound embodiment 1200 with the user's head pitched backward.

Embodiments of the present non-electronic system and method can also incorporate fluids, such as gases an/or liquids, to provide a visual indication of what the vestibular system should be sensing. These fluid systems can also incorporate floats. Fluid based systems can be mechanically simple and the fluid interface, a float or floats, or a pendulum/plumb bob immersed in the fluid can provide a direct visual indication of the gravitational pull and/or inertia being experience by a user. Selection of the viscosity of the fluids and size of the plumbing can provide as much or as little damping as might be desired.

Figure 15A:
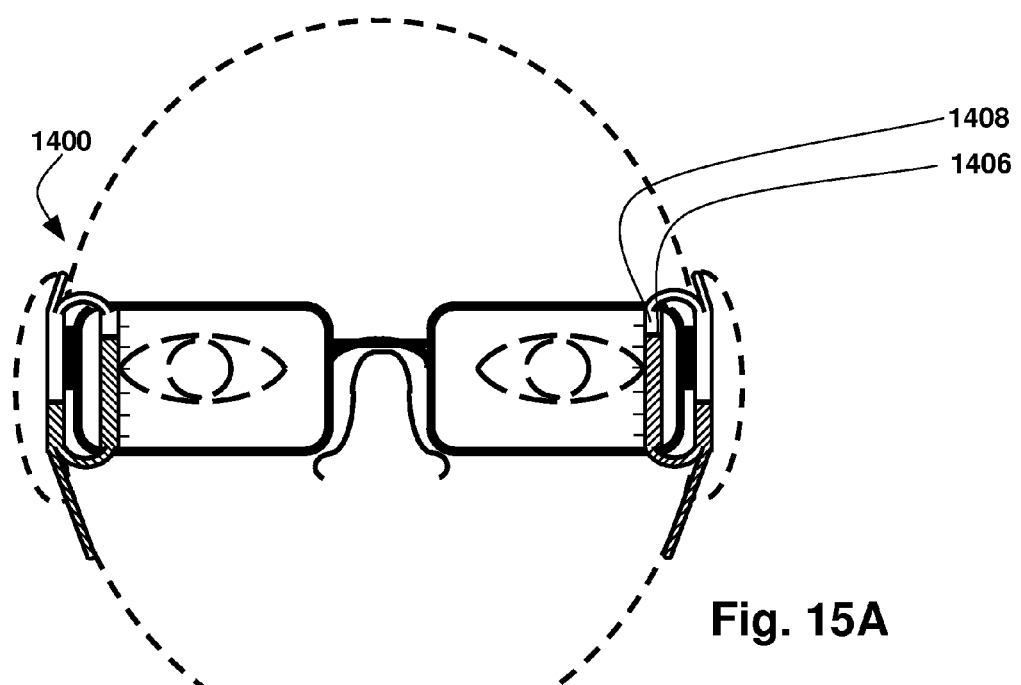
FIG. 15A is a front view of the eyeglasses of FIG. 14A when the user's head is pitched forward.
Figure 15B:
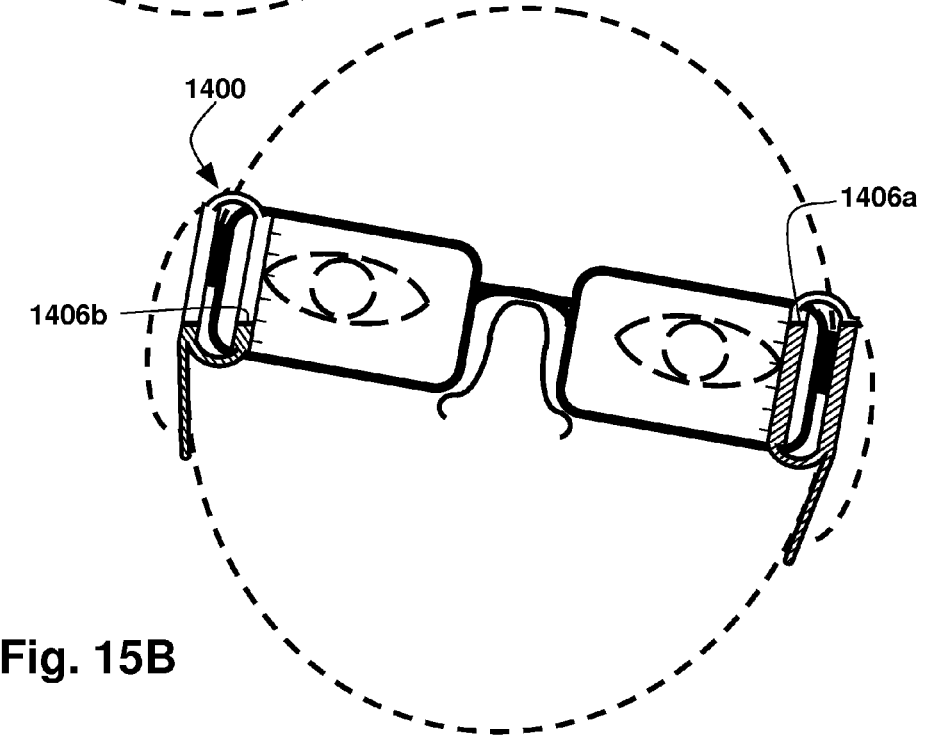
FIG. 15B is a front view of the eyeglasses of FIG. 14A when the user's head is rolled to the left.
Figure 16A:
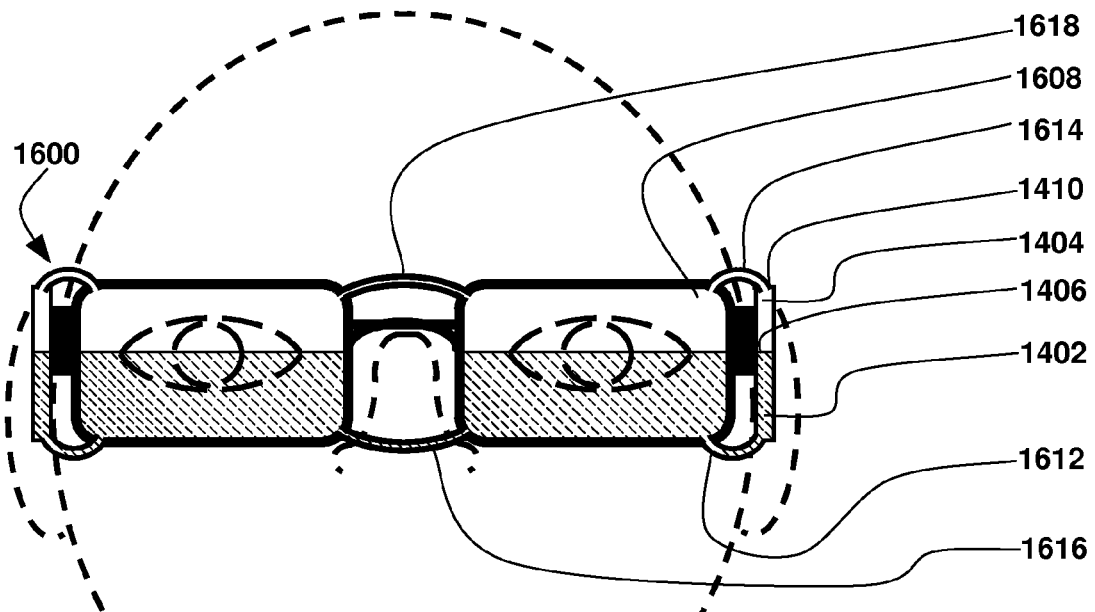
FIG. 16A is an alternate embodiment of the a pair of eyeglasses having a fluid level that moves with pitch and roll of a user's head.
Figure 16B:
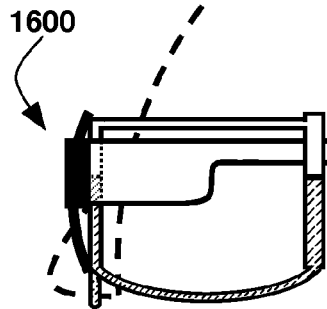
FIG. 16B is a side view of the eyeglasses of FIG. 16A.

Referring to FIG. 14A, FIG. 14B, FIG. 15A, and FIG. 15B, a pair of fluid-level pitch/roll eyeglasses is shown at 1400. The fluid-level eyeglasses 1400 incorporate a first fluid shown at 1402 and a second fluid shown at 1404 that have a fluid-fluid interface shown at 1406. The first fluid 1402 is typically a liquid and the second fluid 1404 can either be a liquid having a lower density than the first fluid 1402 or a gas. The first fluid could be transparent, translucent, or opaque. The second fluid could be transparent, translucent, or opaque. The fluid-fluid interface 1406 may incorporate a float (not shown) that can help increase visibility of the height of the first fluid 1402. The embodiment of the fluid level eyeglasses shown at 1400 uses two clear tubes, one for each eye, shown at 1408 that are located in the user's peripheral vision. The clear tubes are connected to two reservoirs 1410 located on the temples of the eyeglasses in the embodiment shown. Each clear tube 1408 has two connections to its proximate reservoir 1410. One of these connections is a first fluid-reservoir connection 1412 that connects the bottom of the right or left clear tube 1408 with the bottom of the right or left reservoir. The other is a second fluid-reservoir connection 1414 that connects the top of the right or left clear tube to the top of the right or left reservoir. In the embodiment shown in FIG. 14A, FIG. 14B, FIG. 15A, and FIG. 15B, there are also two reservoir-reservoir connections that run behind the user's head. One of these is a first reservoir-reservoir connection 1416 that connects the bottom of the right reservoir to the bottom of the left reservoir. The other is a second reservoir-reservoir connection 1418 that connects the top of the right reservoir to the top of the left reservoir. This embodiment also has a primary head rotation reference symbol 1420 in the form of a scale with horizontal lines placed adjacent to each of the two clear tubes in a location visible to the user. The head rotation reference symbols 1420 will move with the eyeglasses, which move with the head. As shown by FIG. 15A, forward pitch of the head causes the fluid-fluid interface 1406 to rise in the clear tubes 1408 providing visible feedback to the user that the head has pitched forward. The amount of vertical movement of the fluid-fluid level in the clear tubes 1408 as a result of changes in pitch can be controlled in the design of this embodiment through the sizing and placement of the reservoirs relative to the clear tubes. If the clear tubes and the reservoirs have the same cross sectional areas and the reservoirs are located an equal distance behind the center point of the users eyeballs as the clear tubes are in front of the user's eyeballs, the amount of rise and fall of the fluid-fluid interface will correspond with an inertial horizon (i.e. a gravitational artificial horizon if the user is not moving). Increasing the cross sectional area of the reservoirs increases the amplification factor in the clear tubes and decreasing the cross sectional areas decreases the amplification factor. Moving the reservoirs further behind the center point of the users eyeballs increases the amplification factor and moving the reservoirs closer to the center point of rotation about the interaural axis decreases the amplification factor. As shown by FIG. 15B, rotation to the left causes the fluid-fluid interface to rise in the left clear tube 1406*a* and fall in the right clear tube 1406*b* providing visible feedback to the user that the head has rotated to the left.

Figure 17A:
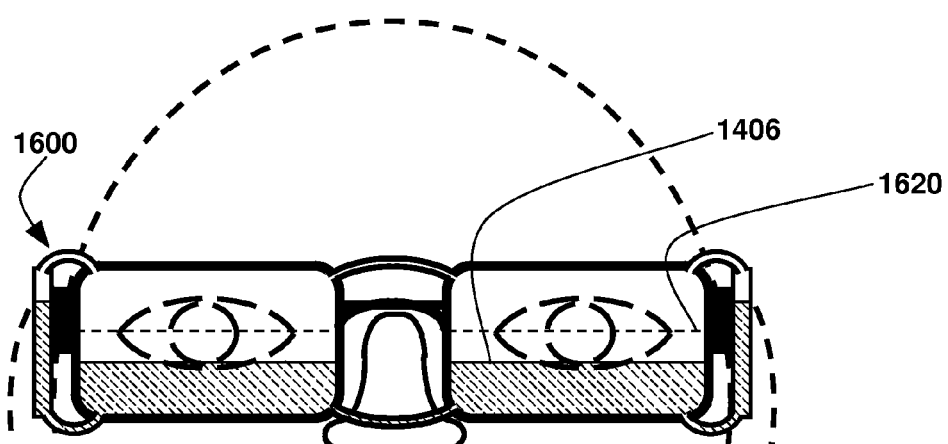
FIG. 17A shows the embodiment of FIG. 16A when the user's head is pitched backward.
Figure 17B:
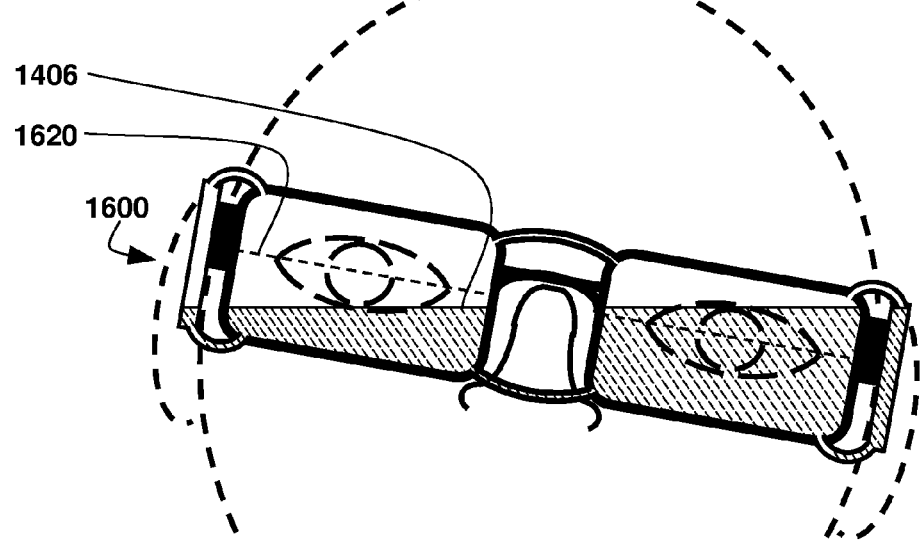
FIG. 17B shows the embodiment of FIG. 16A when the user's head is rolled to the left.

FIG. 16A, FIG. 16B, FIG. 17A, and FIG. 17B, illustrate an alternate fluid-level eyeglass embodiment at 1600. The alternate fluid-level embodiment 1600 has replaced the tubes 1408 of FIG. 14A with fluid-filled windows, shown at 1608. The fluid-filled windows 1608 can have the advantage of more clearly providing visual roll information to the user. They can have the disadvantage that seeing through a liquid can create visually disturbing refraction effects. This alternate embodiment uses the same concepts of a first fluid 1402, a second fluid 1404, and a reservoir 1410. There is a first fluid window-reservoir connection 1612 and a second fluid window-reservoir connection 1614. There is also a first fluid window-window connection 1616 and a second fluid window-window connection 1618 across the bridge of the eyeglasses because this is more convenient than using reservoir-reservoir connections across the back of the head as was done in the embodiment shown in FIG. 14A, FIG. 14B, FIG. 15A, and FIG. 15B. FIG. 17A and FIG. 17B also illustrate that this alternate embodiment uses an alternate primary head rotation reference symbol in the form of a horizontal line etched across the two lenses in the eyeglasses. It should be note that the location of the fluid-fluid for this alternate embodiment does not need to be in the center of the user's line of sight when the user's head is in a neutral (no pitch and no roll) position. The fluid-fluid interface in the neutral position could also be below (or above) the center of the user's line of sight. It should also be noted that the same principles apply in selecting the size and location of the reservoirs in order to provide amplification of the response of the alternate fluid level embodiment to pitch as apply to the embodiment shown in FIG. 14A through 15B.

It should further be noted that concepts illustrated for the fluid-level based eyeglasses can also be used in other head-mounted devices such as helmets and face shields. It is possible to combine elements of the fluid filled embodiments with elements of the roll-element based embodiments and/or the pendulum-based embodiments. For example it is possible to use a fluid-based element (such as a liquid-containing window) for roll and a pendulum for pitch. It is also possible to use many of the primary head rotation reference symbols or secondary head rotation reference symbols with many of the embodiments. It is also possible to build compound embodiments in which a float in a fluid-level system is attached to a linkage that is mechanically coupled to a visible symbol.

It is further possible to implement an embodiment in which the roll indicator is in a separate head worn unit for each eye. For example, contact lenses that have been weighted to orient (as those used for astigmatism) can also have symbology in the form of horizontal or vertical lines or a translucent or transparent region in them to provide pitch feedback to a user. In this case, the reference symbology that is fixed to the user's head may be in a head-worn unit that is separate from the contact lenses. It may further be feasible to make contact lenses that respond to pitch of the eyes to provide pitch information that can also be referenced by the user to a head-worn unit that provides a pitch orientation reference.

The embodiments shown in the attached figures can be illuminated in various ways so that the technology can be used in low levels of light, bright sunlight or darkness. The Embodiments of the present invention can use fiber optics plus tritium, which does not require battery power, other radiochemcials with illumination tubes or chambers. If a battery or solar cell is utilized LEDs can be utilized. If no battery is used such methods as tritium illumination can be used. Tritium illumination is the use of gaseous tritium, a radioactive isotope of hydrogen, to create visible light. Tritium emits electrons through beta decay, and when they interact with a phosphor material, fluorescent light is created, a process called radioluminescence. As tritium illumination requires no electrical energy, it found wide use in applications such as emergency exit signs and illumination of wristwatches. More recently, many applications using radioactive materials have been replaced with photo-luminescent materials. Tritium lighting is made using glass tubes with a phosphor layer in them and tritium gas inside the tube. Such a tube is known as a "gaseous tritium light source" (GTLS), or beta light, (since the tritium undergoes beta decay). The tritium in a gaseous tritium light source undergoes beta decay, releasing electrons, which cause the phosphor layer to fluoresce. During manufacture, a length of borosilicate glass tube which has had the inside surface coated with a phosphor-containing material is filled with the radioactive tritium. The tube is then fused with a $CO_2$ laser at the desired length. Borosilicate is preferred for its strength and resistance to breakage. In the tube, the tritium gives off a steady stream of electrons due to beta decay. These particles excite the phosphor, causing it to emit a low, steady glow. Tritium is not the only material that can be used for self-powered lighting. Other beta particle-emitting radioisotopes can also serve. Radium was used in the past to make self-luminous paint, but has been replaced by tritium, which is less hazardous. Various preparations of the phosphor compound can be used to produce different colors of light. Some of the colors that have been manufactured in addition to the common phosphorus are green, red, blue, yellow, purple, orange, and white. The types of GTLS used in watches give off a small amount of light—not enough to be seen in daylight, but enough to be visible in the dark from a distance of several meter. The average such GTLS has a useful life of 10-20 years. As the tritium component of the lighting is often more expensive than the rest of the watch itself, manufacturers try to use as little as possible. Being an unstable isotope with a half-life of 12.32 years, tritium loses half its brightness in that period. The more tritium that is initially placed in the tube, the brighter it is to begin with, and the longer its useful life. Tritium exit signs usually come in three brightness levels guaranteed for 10, 15, or 20 year useful life expectancies. These light sources are most often seen as "permanent" illumination for the hands of wristwatches intended for diving, nighttime, or tactical use. They are additionally used in glowing novelty key chains and in self-illuminated exit signs. They are favored by the military for applications where a power source may not be available, such as for instrument dials in aircraft, compasses, and sights for weapons. Tritium lights are also found in some old rotary dial telephones, though due to their age they no longer produce a useful amount of light. Tritium lights or beta lights were formerly used in fishing lures. Some flashlights have slots for tritium vials so that the flashlight can be easily located in the dark. Tritium is used to illuminate the sights of some small arms. The electrons emitted by the radioactive decay of the tritium cause phosphor to glow, thus providing a long lasting (several years) and non-battery-powered firearms sight which is visible in dim lighting conditions. The tritium glow is not noticeable in bright conditions such as during daylight however. As a result, some manufacturers have started to integrate fiber optic sights with tritium vials to provide bright, high-contrast firearms sights in both bright and dim condition Because tritium in particular is an integral part of certain thermonuclear devices (though in quantities several thousand times larger than that in a keychain), consumer and safety devices containing tritium for use in the United States are subject to certain possession, resale, disposal, and use restrictions. Devices such as self-luminous exit signs, gauges, wrist watches, etc., which contain small amounts of tritium are under the jurisdiction of the US Nuclear Regulatory Commission, and are subject to possession, distribution, import and export regulations found in 10 CFR Parts, 30, 32 and 110. They are also subject to regulations for possession, use and disposal in certain states. They are readily sold and used in the US and are widely available in the UK and are regulated in England and Wales by environmental health departments of local councils. Tritium lighting is legal in most of Asia and Australia. While these devices contain a radioactive substance, it is currently believed that self-powered lighting does not pose a significant health concern. Encapsulated tritium lighting devices, typically taking the form of a luminous glass tube embedded in a thick block of clear plastic, prevent the user from being exposed to the tritium at all unless the device is broken apart. Tritium presents no external radiation threat when encapsulated in non-hydrogen-permeable containers due to its low penetration depth, which is insufficient to penetrate intact human skin. The primary danger from tritium arises if it is inhaled, ingested, injected or otherwise absorbed into the body. This results in the emitted radiation being absorbed in a relatively small region of the body, again due to the low penetration depth. The biological half-life of tritium—the time it takes for half of an ingested dose to be expelled from the body—is low, at only 12 days. Tritium excretion can be accelerated further by increasing water intake to 3-4 liters/day. Direct, short-term exposure to small amounts of tritium is relatively harmless. If a tritium tube should break, one should leave the area and allow the gas to diffuse into the air. Tritium exists naturally in the environment, but in very small quantities. Options include tiny gas lights (borosilicate glass capsules). Some watches are advertised to possess "always visible technology." The watch hands and markers contain tritium insets which provide permanent luminescence, as opposed to phosphorescent markers used in other watches, which must be charged by a light source. The tritium in a gaseous tritium light source undergoes beta decay, releasing electrons which cause the phosphor layer to fluoresce. During manufacture, a length of borosilicate glass tube which has had the inside surface coated with a phosphor-containing compound is filled with the radioactive tritium. The tube is then fused with a $CO_2$ laser at the desired length. Borosilicate is used for its strength and resistance to breakage. In the tube, the tritium gives off a steady stream of electrons due to beta decay. These particles excite the phosphor, causing it to emit a low, steady glow. Tritium-filled luminous tubes entered the market in the '90s, and while their multi-year illumination makes them a good choice, their relatively low brightness can be difficult to see in partially lit conditions, or immediately after moving from a brightly lit to a dark environment. Starting in 2003, Reactor developed a proprietary method of applying a unique Swiss material called Superluminova that makes other watches the brightest and longest-lasting phosphorescent watches in the world. However, while Superluminova is at least five times brighter than tritium after being charged in the light, that brightness fades to below that of tritium over several hours. Never Dark™ was the first technology to combine the intense brightness of Superluminova with the multi-year longevity of tritium, providing optimal illumination under all lighting conditions. Because it can take up to 30 minutes for the human eye to fully adjust to the dark, Superluminova's intense peak brightness makes a Never Dark™ watch easily visible during that initial period. This can be even more important when moving repeatedly from light to dark (such as when going below deck on a boat during the day), as the Superluminova will continually recharge and the eye will not have time to adjust. In situations where the watch will remain in the dark for many hours, the tritium will remain visible for years, even if the watch is never returned to the light. While tritium remains at a constant level, Superluminova gets extremely bright then fades over several hours, but recharges very quickly when re-exposed to light. Never Dark® is the only watch illumination to "self-adjust" to conditions, with a response curve similar to that of the human eye. At its peak, the glow of Superluminova is easily visible, even at dusk or in difficult, partially lit conditions. With a full charge, it produces five to ten times the light output of tritium. But, as that brightness fades, the tritium will continue to glow for at least ten years. Unlike radioactive isotopes that have been used on watches in the past, tritium poses no health risk to the wearer or to the workers who assemble the watches. Tritium's radioactive decay produces only weak beta particles that are contained completely within the sealed glass tubes. Even if exposed, the beta particles do not possess enough energy to penetrate the outer layer of human skin.

Embodiments of the present invention can further include one or more optical elements. The term optical element as used in this disclosure includes lenses, mirrors, prisms, beam splitters, retro-reflectors, fluids, other transmissive or transparent media, and any other device that can change the appearance or apparent location of an image. The optical elements can have a variety of coatings. The optical elements can be used in variety of combinations. The optical elements may have surfaces that are flat, concave, convex, and/or any other shape capable of being understood by anyone skilled in the art. The optical elements can be used for a variety of functions including focusing and/or defocusing. As examples of combinations, embodiments of this invention can use single or multi-element mirrors, single or multi-element lenses, combinations of a mirror or mirrors with a lens or lenses, and combinations of a mirror or mirrors and/or a lens or lenses, with other optical elements, such as those elements previously described.

Lenses are transmissive optical elements or modules that use refraction to affects the focus of a light beam. A lens can focus light to form an image, unlike a prism, which refracts light without focusing or a mirror which reflects light. A simple lens consists of a single piece of material. Simple lenses can be subject to optical aberrations which can be compensated for by using a combination of simple lenses with complementary aberrations. A compound lens is a collection of simple lenses of different shapes and made of materials of different refractive indices, arranged one after the other with a common axis. One of the reasons that lenses might be combined is that whatever good the performance of an aspheric lens may be in monochromatic light, it cannot cover wide spectral range because refractive index of glass varies with wavelength, causing chromatic aberration. The common solution to this problem is the so-called achromatic doublets, which is a pair of cemented convex and concave lenses of different refractive indices. The achromatic doublet may be designed either for best chromatic compensation or for best spherical aberration performance.

A lens or lenses can be used to facilitate close distance focusing on the symbology described earlier in this disclosure. There are a many different lens configurations available which can provide a focused central image. It can be desirable to keep the mounting of the device close to the eye and avoid a large projection away from the eye and lens surface. To accomplish this, the lens can have a more complex design property and multiple lenses can be used, mounted together or separated from each other. A mirror, prism, or beam splitter can also be used to project the image to the visual field and in combination with the lens or lenses.

To maintain required features of the displayed image or symbology, the lens or lenses can move in response to gravity. This can be accomplished by having a weighted lens or lens assembly, with the heavier component on the bottom that is mounted in a way that it can rotate on bearings that have little to no friction. The lens could rotate relative to the framework with "frictionless" bearings, as the head or body rotates, to always provide a true horizontal area, which the user can focus on when experiencing motion or motion sickness. Alternatively, fluid can be used in combination with a lens to visualize the image, which remains horizontal with pitch and roll movements.

Achromatic Lenses are examples of lenses used to minimize or eliminate chromatic aberration caused by light at different frequencies that are bent differently by the index of refraction of a lens composed of only one material. Achromatic Lenses are ideal for a range of applications, and often designed by either cementing two elements together or mounting the two elements in a housing. Achromatic lenses can be used to create smaller spot sizes than comparable chromatic lenses.

Aspheric Lenses can be preferable lenses and are used to eliminate spherical aberration in a range of applications, including bar code scanners, laser diode collimation, or OEM or R&D integration. Lens configurations which include an aspheric lens can provide excellent central resolution of the visualized image at a closer focal distance from the eye than an equivalent spherical lens. Aspheric lenses can accomplish more in a single element design than spherical lenses, which helps minimize the number of lenses found in multi-lens optical assemblies. Aspheric lenses have a more complex front surface that gradually changes in curvature from the center of the lens out of the edge of the lens. In an aspheric lens the surface of the lens is "folded open" in the peripheral areas so that the surface structure deviates from the spherical shape. All rays coming from the distance meet again at one point. The spherical aberration is corrected. A positive side effect of this flattening is that it leads to thinner and lighter lenses. This effect is most evident with high plus powers. In this case, the reduction of the center thickness also leads to a reduced magnification effect. An aspheric lens can be coated with a range of the Ultraviolet (UV) spectrum, visible light, or Infrared (IR) spectrum.

The aspheric lens can be mounted in a lightweight holder to minimize size and weight. This assembly can further include a reticle, feature and/or other images or symbology. The lens assembly can be incorporated in a transparent plastic lens framework. The lens aperture may vary from 4 mm to 10 mm. If a reticle is incorporated, the reticle diameter is also variable, but generally can be 6-6 mm to allow adequate field of view. The lens and other optical elements can be attached to the eyewear or can be incorporated into the eyewear. A clip on feature can allow the assembly to be closer to the pupil when needed. If the assemble in incorporated into the lens it can move/slide into a more appropriate position when needed. This would then accommodate the eye/pupil position to enhance human performance. Specifically this can be done with a housing for fitting an aspheric lens and modified reticle.

Regardless of the optical element or combination of optical elements used the goal of the optical assembly is to provide a clear picture of the symbology/image/feature/reticle visualized to mitigate the symptoms of motion sickness/dizziness/disorientation. The eye worn device can then be worn in any environment, whether it be virtual, augmented, real life or in active situational activities.

Beam-splitters are another optical element that can be used in embodiments of the present invention. The two most commonly used types of beam-splitters are the beam-splitting plates and cubes. Generally, they are designed for 45 angle of incidence and transmission ratios 50/50, 70/30, or 90/10%. The beam-splitting cubes may be either polarizing or non-polarizing. The beam-splitting plate has only three advantages over the cube: lower price, less aberration when installed in a converging beam, and possibility to completely eliminate the ghost beam when the plate has a wedge. Aberration is smaller simply because the plate is much thinner than the cube. In all the other components the cube is better: better spectral uniformity of the reflection coefficient, smaller difference between transmission coefficients for sand p-polarization, less ghosting, no displacement, easier to mount, negligible deformation under mechanical stress. In a beam-splitting plate, the beam reflects from the interface between the air and glass—two materials with very different refractive indices (1.0 and 1.5).

Reticles. For a person experiencing motion sickness, vision induced motion sickness dizziness, disorientation or vertigo, visual fixation on a stable point will mitigate or abort the symptoms. A stable horizontal line has been found to be effective for a person experiencing motion sickness. Embodiments of other optical elements of the present invention can utilize a horizontal line, symbols, reticles and/or other features and can further include a center mark on the horizontal line for the user to focus on when experiencing symptoms of motion sickness, vision induced motion sickness, dizziness, vertigo or disorientation. Additionally, embodiments of the present invention can provide pitch and roll information about the user's position to enhance the user's orientation in space. The horizontal area will always remain horizontal and enable the user to focus on a stable point of reference. This horizontal line can be comprised of symbols, features and/or lines and may resemble the cross hairs of a reticle. Reticles may be etched on the lens or/lenses.

Etched glass reticles can have floating elements (such as circles or dots), which do not cross the reticle. Reticles can have complex sections designed for other use. Reticles can be printed or etched on a transparent material such as glass or plastic. Reticles on a transparent material can be less durable than wire reticles, and the surface of the transparent material can reflect some light (about 4% per surface on uncoated glass) lessening transmission through the lens system, although this light loss is near zero if the glass is multi-coated. The horizontal line or reticles may be illuminated, either by a plastic or fiber optic light pipe collecting ambient light. Some illumination sources can use the radioactive decay of tritium for illumination, which can work for 11 years without using a battery. Red is the most common color used for illumination, as it is the least destructive to the night vision, but some can use green or yellow illumination, either as a single color or changeable via user selection. The reticle may be located at the front or rear focal plane (First Focal Plane (FFP) or Second Focal Plane (SFP) and multiple lenses, beam splitters or mirrors may be used to adjust the focal length.

Figure 18A:
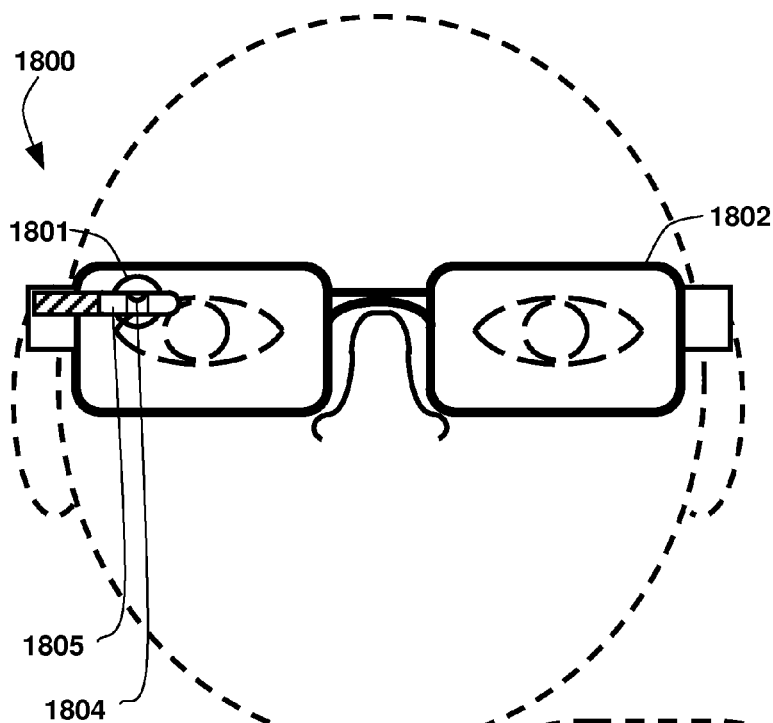
FIG. 18A shows a front view of a pair of eyeglasses that uses a lens to focus on a fluid-filled roll sensor.
Figure 18B:
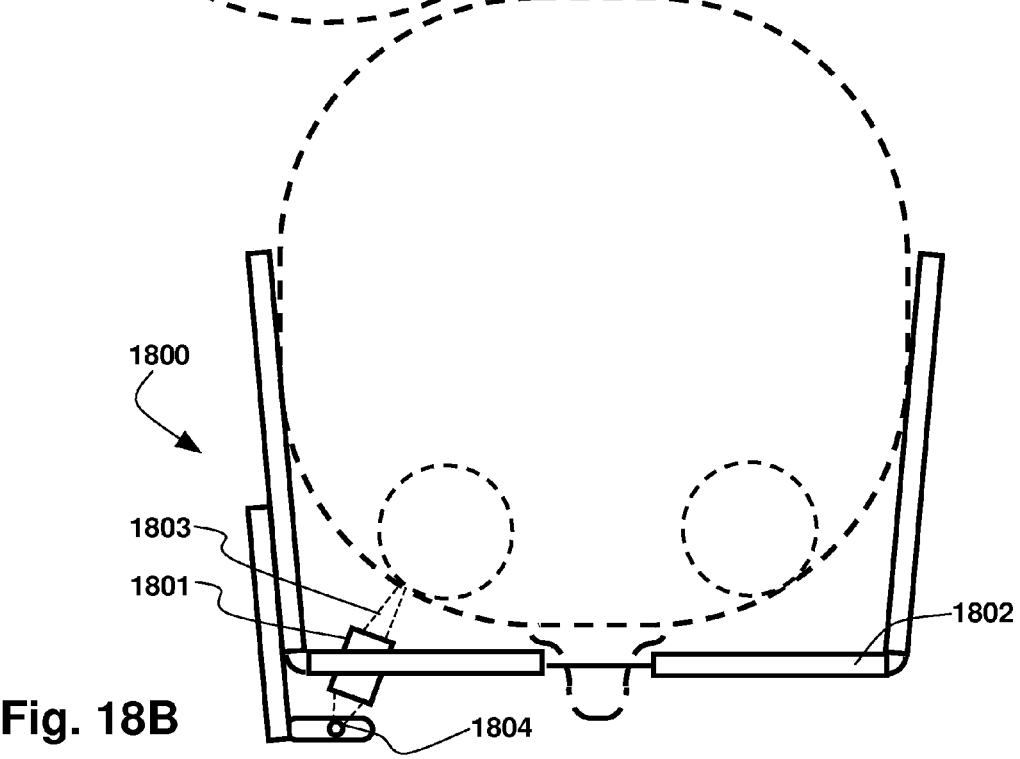
FIG. 18B shows a top view of the embodiment of FIG. 18A.

FIG. 18A and FIG. 18B show an embodiment of the present invention that uses a lens. FIG. 18A is a front view and FIG. 18B is a top view. In the embodiment shown at 1800, the lens housing 1801 is mounted in a pair of glasses 1802. The lens body 1801 comprises a lens (not visible in these views) that bends the optical path 1803 to allow the user to focus on a bubble 1804 in a liquid reservoir 1805. The advantage of the embodiment shown in FIG. 18A and FIG. 18B over the embodiments previously shown is that a user can more easily focus on the orientation indicator, a fluid filled roll sensor in this example. It should be noted that this concept of using a lens to focus at short distance could be applied to all of the embodiments previously described in this disclosure.

Figure 19A:
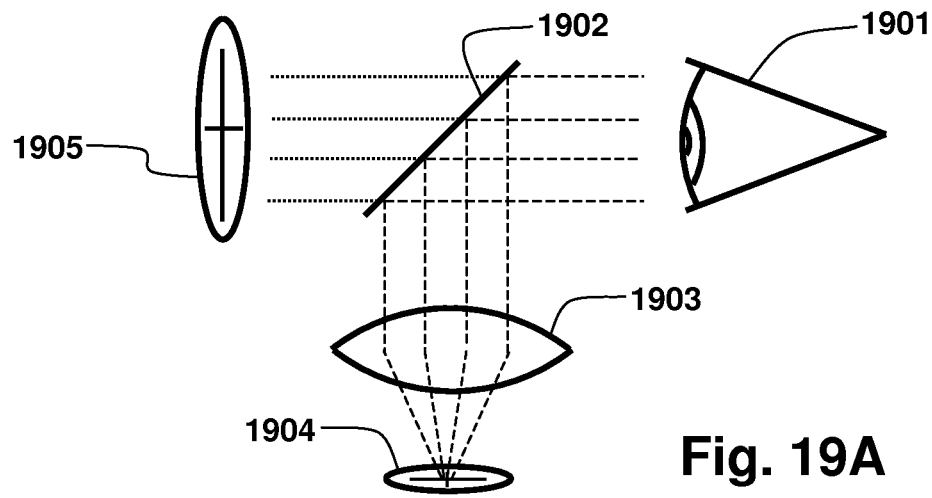
FIG. 19A shows the use of a mirror and a lens to focus at a short distance and in a different orientation from a viewer's normal line of sight.
Figure 19B:
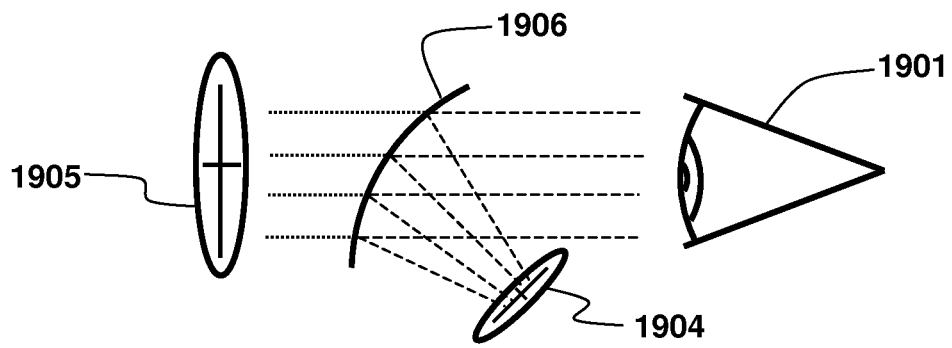
FIG. 19B shows the use of a concave mirror to focus at a short distance and in a different orientation from the viewer's normal line of sight.
Figure 19C:
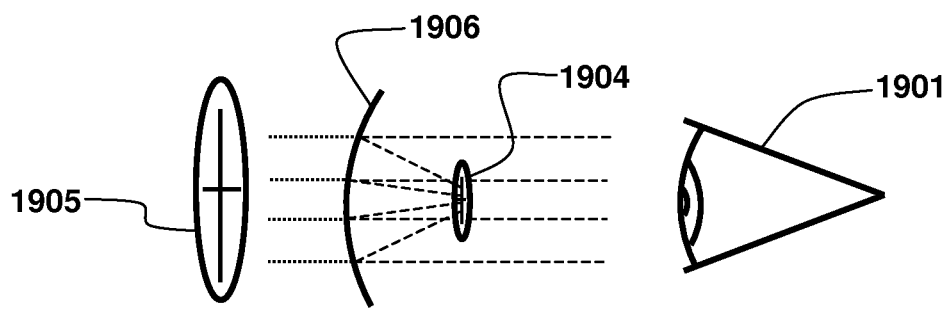
FIG. 19C shows the use of a concave mirror to focus at a short distance in the viewer's normal line of sight.

FIG. 19A, FIG. 19B, and FIG. 19C show three types of reflector sights that produce virtual images of reticles. FIG. 19A uses a collimating lens (CL), shown at 1903, and a beam splitter, shown at 1902, to superimpose an apparent virtual image at infinity, shown at 1905, of an actual image, shown at 1904, of a reticle. FIG. 19B uses a half silvered concave mirror (CM), shown at 1906, as the collimating optics to view an actual image 1904 that is an offset. FIG. 19C uses a half silvered concave mirror (CM) 1906 as the collimating optics with the actual image 1904 between the mirror and the observer. Apparent images 1905 of collimated reticles such as those shown in FIG. 19A, FIG. 19B, and FIG. 19C are produced by non-magnifying optical devices such as reflector sights (often called reflex sights) that give the viewer an image of the reticle superimposed over the field of view, and blind collimator sights that are used with both eyes. Collimated reticles are created using refractive or reflective optical collimators to generate a collimated image of an illuminated or reflective reticle.

Reflector sight or reflex sight is another optical element device that allows the user to look through a partially reflecting glass element and see an illuminated projection of an image superimposed on the field of view. These sights work on the principle that anything at the focus of a lens or curved mirror (such as an illuminated reticle) will look like it is sitting in front of the viewer at infinity. Reflector sights employ some sort of "reflector" to allow the viewer to see the infinity image and the field of view at the same time, either by bouncing the image created by lens off a slanted glass plate, or by using a mostly clear curved glass reflector that images the reticle while the viewer looks through the reflector. Since the reticle is at infinity, it stays in alignment with the device the sight is attached to regardless of the viewer's eye position, removing most of the parallax and other sighting errors found in simple sighting devices. The image is reflected off some form of angled beam splitter or the partially silvered collimating curved mirror itself so that the observer (looking through the beam splitter or mirror) will see the image at the focus of the collimating optics superimposed in the sight's field of view in focus at ranges up to infinity. Since the optical collimator produces a reticle image made up of collimated light, light that is nearly parallel, the light making up that image is parallel with the axis of the device it is aligned with, i.e. with no parallax at infinity. The collimated reticle image can also be seen at any eye position in the cylindrical volume of collimated light created by the sight behind the optical window.

Figure 20A:
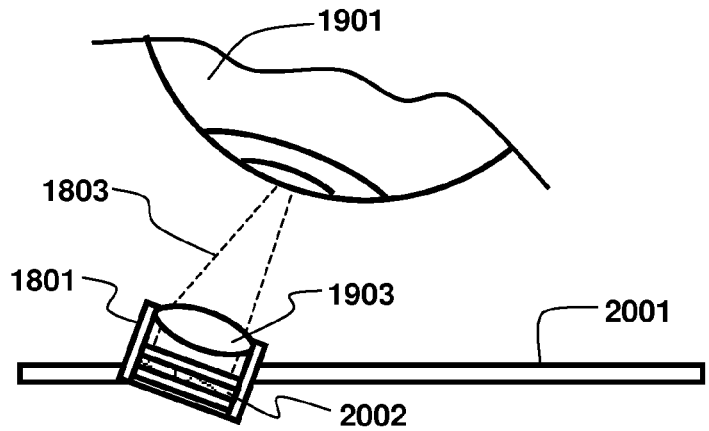
FIG. 20A shows a top schematic view of a housing that holds a lens, a fluid filled chamber, and reticle, wherein the housing is mounted in an eyeglass.
Figure 20B:
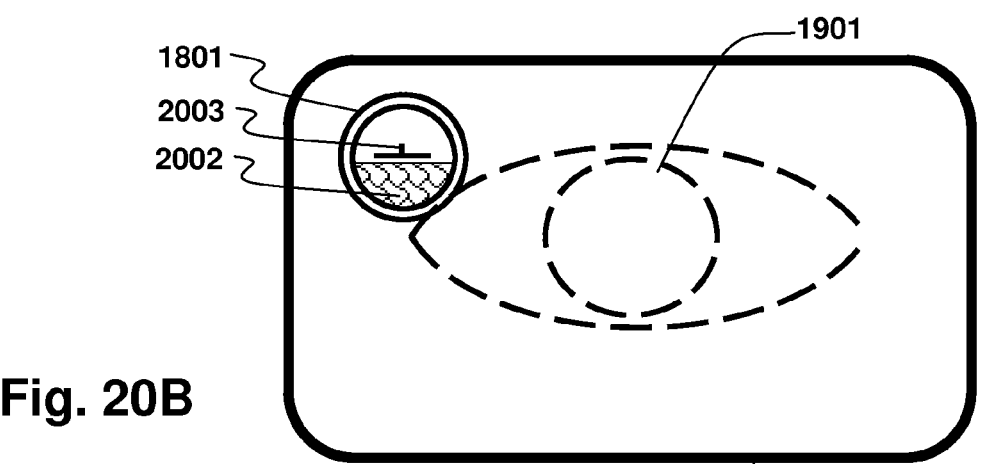
FIG. 20B shows a front view of the embodiment of FIG. 20A.
Figure 20C:
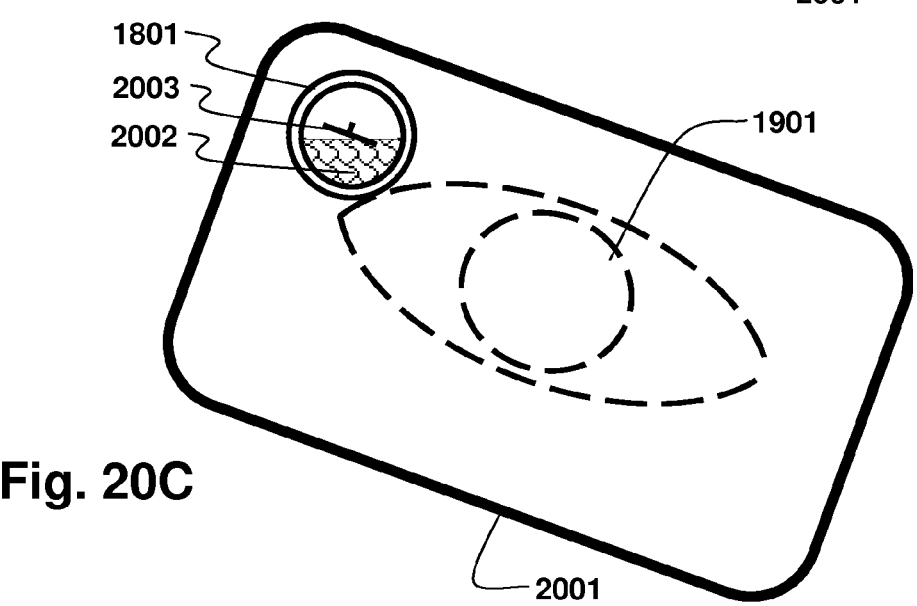
FIG. 20C shows the embodiment of FIG. 20A and FIG. 20B when the user's head is rolled to one side.

FIG. 20A shows a top schematic view of a housing 1801 that holds a lens 1903, fluid-filled chamber 2002, and a reticle, wherein the housing 1801 is mounted in an eyeglass, shown at 2001. The optical path 1803 from a user's eye 1901 to the fluid-filled chamber 2001 is also depicted in FIG. 20A. FIG. 20B shows a front view of the embodiment of FIG. 20A and FIG. 20C shows this front view when the user's head is rolled to one side. In addition to the elements shown in FIG. 20A, the two front views shown in FIG. 20B and FIG. 20C also show the relationship between the fluid 2002 and the reticle 2003 when the user's head is rolled to one side. The reticle 2003 rolls with the head and the fluid 2002 stays level due to gravity or inertia. In the system shown in FIG. 20A, FIG. 20B, and FIG. 20C, the housing 1801 can be transparent and just large enough to hold the lens 1903, which is convex. The lens could be 6 mm and is there to allow the eye 1901 to focus at a close distance on the reticle 2003 and the level of the fluid 2002. The reticle 1801 could be an image on the reticle or on one of the transparent or translucent surfaces of the fluid-filled chamber 2002.

FIG. 21A shows an embodiment using a mirror, lens, ball, and reticle to provide both pitch and roll information off-bore of the user's normal line of sight. This embodiment, shown at 2100 comprises two orientation modules, shown from the top at 2101. The optical paths from the user's eyes are shown at 1803. FIG. 21B shows a side view of the orientation module 2101 to show how the optical path 1803 from the eye 1901 enters the housing 1801, is bounced off of a flat mirror 2102, passes through a lens 1903 to view a rolling element 1130. The rolling element 1130, in the form of a sphere, can roll on the convex surface at the bottom of the housing to indicate both pitch and roll of the orientation module 2101, and therefore the system 2100 and therefore the user's head. FIG. 21C shows a bottom view of the orientation module 2101 to illustrate how the housing of the orientation module 2101 can further comprise a reticle 2003 that provides a reference for the location of the rolling element 1130 as the user's head rotates in the pitch and roll directions. The housing 1801 could be made out of a Plexiglas or other transparent material is machined to hold the lens 1903 on one end and the reticle on the other with the spacing such that the reticle is focused to the eye. This can be a module approximately 14 mm long that could be mounted to eyeglasses in some position off axis to the central vision. This could be attached to the eyeglasses or incorporated into the framework or transparent portion of the eyeglasses. The orientation of the mounting can be adjusted to accommodate for the user's anatomy of the face and eye position. Specifically, an opening can exist in the plastic or other type of lens of an eyeglass to accept and angular position the optic at the right distance off axis.

Figures 22A, 22B:
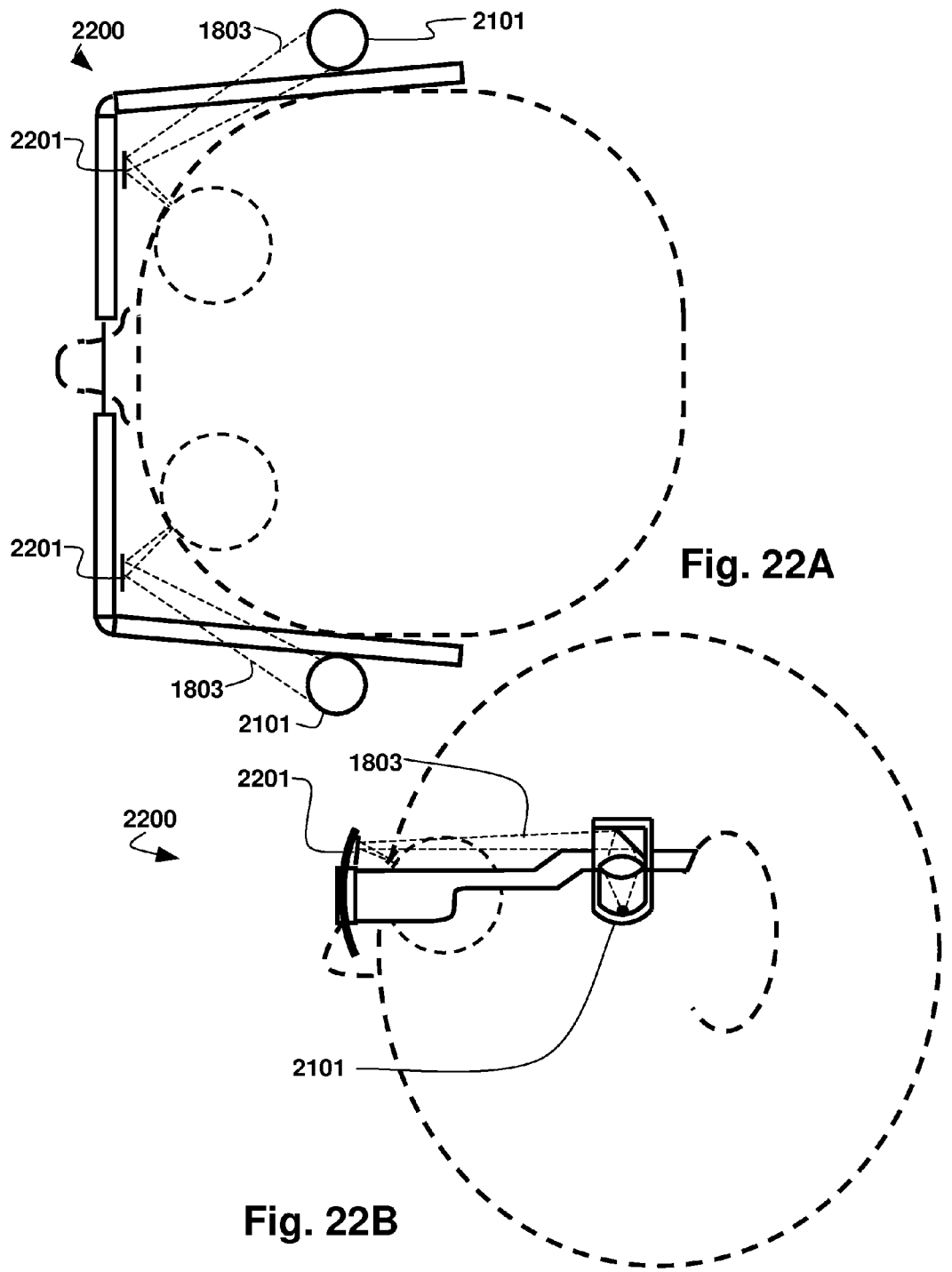
FIG. 22A shows a top view of an embodiment using rear view mirrors and the orientation module shown in FIG. 21B.
FIG. 22B shows a side view of an embodiment using rear view mirrors and the orientation module shown in FIG. 21B.

FIG. 22A and FIG. 22B show two views of an embodiment 2200 that uses rear view mirrors 2201 in conjunction with the orientation module of FIG. 21A, FIG. 21B, and FIG. 21C. By having rear view mirrors 2201, the optical path 1803 allows for (1) a greater distance between the eye and the reticle and rolling element, (2) placement of the orientation modules further back and in a less visually obtrusive location, and (3) the use of two mirrors, which helps to make the motion of the roller in the housing move in a more intuitive way for the user. Both pitch and roll feedback can be provided to the user in this embodiment.

The mounting of the embodiments described here can be in the form of a clip on device to the framework of the eyewear, a fixed or detachable method can also be use with a pivot, swivel or tilting mechanism to position the system or device into the visual field. The device can be positioned in the central visual field of view or off the central visual field (e.g. "off bore"). The positioning within the visual field can be manually selected, adjusted and fixed to the framework of the eyewear. The mounting position can be adjusted to whatever position the user prefers. For example, if the user is experiencing motion sensitivity, the device may be preferred to be positioned more closely to the center of the visual field and if there is no motion experienced the preferred position may be "off bore". The mounting of the system or device can also be incorporated in the eyewear lens. This can be seen as a fixed mounting through a perforation in the eye worn lens or an opening in the lens of a variable length will allow movement of the device, within the lens, for proper positioning depending on the user's preference and the anatomy of the eye position. The mounting of the device system can also allow for tilting anteriorly and posteriorly or laterally (e.g. the device can be pitched forward or backward and can be rolled to either side) in order to position the visualized image well. Inertial mounting of the system device can also allow the viewed horizontal image to move as the head rolls to the right or left. When the head rolls to the left horizontal image can be seen to remain horizontal. The mounting of the device can also allow for adjustments in focal length, if the focal length needs to be changed.

Additional further embodiments can include:
A. A feature to manually adjust focal length;
B. Operation that comprises the ability to detect at least 30 degrees of pitch and 30 degrees of roll;
C. A feature that provides pitch and roll data;
D. The incorporation of multiple lenses, mirrors, prisms, and/or split beams to provide a clear image to the user;
E. The use of frictionless ball bearings or fluids to maintain the horizontal line/image/feature/symbology in a horizontal plane
F. An opening in the lens that can provide a method of sliding adjustment for positioning of the device, to move it either into "bore site or off bore site";
F. A configuration in which only the horizontal image is seen in the lens and the frame of the system and/or eye wear provides pitch and roll information; and
G. A configuration in which the device is combined with an electronic head-worn eye tracker, head tracker, a head-worn display, and/or transducers capable of obtaining and displaying biometric information.

Applications for the present technology can include a variety of provocative motion environments such as vehicle use, an AR (augmented reality environment), a multi-dimensional environment, a synthetic or computer generated synthetic environment, and/or a visual induced environment, such as watching motion while the user is motionless. A more detailed description of some of these examples and some other examples are:
A. Vehicles. The most obvious use for this invention is to prevent motion sickness, spatial disorientation or visually induced motion sickness symptoms with any type of vehicular use, whether it moves on the ground, in air, or on water. In such an environment physical or visual movement alters our normal sense of perception and visual causing symptoms of sickness and resulting in loss of human performance activities or decay in physical and or perceptual normalcy. Examples of vehicular activities where the invention has benefit opportunities include:

(i) Operators and passengers in commercial, general aviation, and military fixed wing aircraft including tanker, airlift, support, and fighter aircraft can employ the head-worn, eye-worn embodiments of the present technology to improve comfort, mission-effectiveness, and human performance. SD/MS causes degradation of human performance (affecting cognitive and motor skills), with resultant loss of expensive equipment and human life. Embodiments of the present invention can provide the visual cues necessary to combat SD in the civil aircraft flight environment and control the motion sickness in the other flight personnel to enhance their human performance. Passengers in commercial air carriers, business and general aviation aircraft routinely experience motion sickness from vestibular upset and loss of visual cues. Embodiments of the present invention can prevent or lessen the motion sickness/visually induced motion sickness for passengers aboard all type of civil aircraft.

(ii) Helicopters. Rotary wing aircraft are particularly capable of generating high motion provocative environments due to extreme vibration, the visual flash of the rotor blades in various lighting conditions and unique maneuvering capabilities. One more specific example is Flash Vertigo. There are many case examples where helicopter operators/passengers have encountered extremely adverse physical effects due to the flickering or flashing of light through the rotating blades of the helicopter. Some of the most severe have resulted in motion sickness, spatial disorientation or vertigo. Use of embodiments of the present invention can reduce the negative effects associated with the strobe effects of rotor wing vehicles. It can also help during brown-out when rotary wing operators can experience loss of visual cues and a sensation of downward velocity increase and/or disorientation when landing in blowing or loose sand environments.

(iii) Ships, boats, and other marine vessels. Sailors stationed aboard naval ships and merchant marine vessels have long been susceptible to motion sickness associated with the vessel movements that occur during aggravated sea states. It is estimated that nearly every person ever stationed aboard a marine vessel for a prolonged status has suffered mild to debilitating seasickness. Embodiments of the present invention can prevent, alleviate, and/or mitigate the symptoms of seasickness aboard ships. Naval aircrew members assigned aboard ships who engage in flight simulator training on those ships often are affected by motion sickness. This occurs because the motion of the ship and associated vestibular stimulus creates a mismatch with visual cues viewed in the simulator. Additionally the simulator results in a loss of visual cues regarding the shipboard environment. This technology will prevent/mitigate motion sickness that occurs during shipboard flight simulator training Embodiments of the present invention can also be effective in controlling motion sickness associated with leisure ship board cruises.

(iv) Land vehicles. One example is reading during vehicular travel. Many people become carsick when sitting in the back of a moving vehicle with reduced visual cues and increased vibration and even more still when attempting to read in this motion provocative environment. Embodiments of the present invention can provide visual cues to counteract the loss of the normal visual cues that would mitigate SD/MS, with the stimulation of the inner ear and offset the effect of vibration in the ground transportation environment (v) Space: Micro-gravity and Re-entry Rehabilitation. Embodiments of the present invention can space sickness by providing visual cues to offset the loss of proprioception and orientation due to loss of gravitation. Embodiments of the present invention can also reduce the time to re-acclimate to the terrestrial environment by providing strong visual cues to help orientation in conjunction with the increase in cues provided by reintroduction of gravitation.

(vi) Theme parks and movie theatres. It is highly common for tourists visiting theme parks to become disoriented or experience motion sickness riding them park rides. This is due to the nature of the attractions themselves that either generate extreme motion provocative environments or provide visual cues that have the same effect by using extremely provocative visual displays, simulated displays, 3-D, 4-D or 5D displays, mirroring or reflection environments. Embodiments of the present invention can prevent the associated sickness by providing overriding visual cues that show the true orientation of the passenger with respect to the ground. The head/eyewear is effective in countering motion sickness, visually induced motion sickness, and spatial disorientation in rides that use high fidelity visual displays since the passenger would be able to verify his/her actual position.

(vii) Sports and recreation. In nearly every sports activity that features the loss of visual cues or motion provocative environment such as sailing, rock climbing, and auto racing participant's remark on the loss of situation awareness, disorientation or occasional motion sickness. It is expected the invention will prevent symptoms similarly as described above in these environments by providing strong visual cues to counter the effects of sensory mismatch associated with these motion provocative environments. Similarly, in offshore fishing it is highly common for at least one person in the party of any recreational offshore fishing boat to become seasick. As with regard to ships and boats, embodiments of the present invention can be effective in the prevention and control of motion sickness in person aboard small marine vessels.

B. Stroboscopic/Stereoscopic viewing. Different types of stereoscopic display viewing or stroboscopic viewing can induce eye symptoms as described above and cause sickness symptoms. This technology can lessen the visual fatigue/visual discomfort and other visual symptoms as well as the associated visually induced motion sickness.

C. Simulators and Displays.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims. For example, embodiments of the present invention can include fluids or pendulums. A number of variations and modifications of the disclosed embodiments can also be used. The principles described here can also be used for other applications. While the principles of the disclosure have been described above in connection with specific apparatuses and methods, it is to be clearly understood that this description is made only by way of example and not as limitation on the scope of the disclosure.

What is claimed is:

1. A non-electronic system for providing visual orientation information, the system comprising:

a head attachment unit configured for attachment to a head of a person;

an optical element selected from the group of a lens, a mirror, a beam splitter, and a prism wherein the optical element is configured to be visible to the person;

an orientation reference symbol configured to be visible to the person when viewing the optical element, wherein:
the symbol is fixedly coupled to movement of the head attachment unit whereby the symbol is configured to be in a fixed visual position for the person when the person's head moves; and
the symbol comprises a reference element selected from the group of a pitch reference element and a roll element;

an indicator selected from the group of a pitch indicator and a roll indicator, wherein:
the indicator is configured to be visible to the person when viewing the optical element;
the indicator moves in response to rotation of the head attachment unit about an orientation selected from the group of an interaural axis and a naso-occipital axis of the person;
the indicator is responsive to an inertial device selected from the group of a pendulum attached to the unit, a rolling element retained in the unit, and two fluids in a reservoir in the unit;
movement of the indicator does not comprise a response from an electro-mechanical sensor selected from the group of an accelerometer, a gyroscope, an acoustic detector, a magnetic detector, and an optical detector; and
movement of the indicator does not require the use of electricity; and
movement of the indicator occurs in a normal field of view of the person.

2. The system of claim 1 wherein the system is suitable for use in a vehicle.

3. The system of claim 1 wherein the system does not use a magnet.

4. The system of claim 1 wherein the symbol further comprises an eye fixation element whereby the person can focus on the eye fixation element to minimize a physiological effect selected from the group of vertigo, motion sickness, vision-induced motion sickness, motion intolerance, and spatial disorientation resulting from sensory mismatch between a person's visual, vestibular, and proprioceptive organs.

5. The system of claim 1 wherein:
the unit comprises a head-worn module selected from the group of eyeglasses, a helmet, and a face shield;
the head-worn module comprises a non-opaque region through which a person can see directly ahead; and
the non-opaque region comprises a material selected from the group of glass and a polymer.

6. The system of claim 1 wherein the indicator is detachably attached to the unit.

7. The system of claim 1 wherein:
the optical element further comprises:
a left eye optical element; and
a right eye optical element;
the orientation reference symbol further comprises:
a left eye orientation reference symbol selected from the group of a left eye pitch reference element and a left eye roll reference element; and
a right eye orientation reference symbol selected from the group of a right eye pitch reference element and a right eye roll reference element;

the indicator further comprises:
a left eye indicator selected from the group of a left eye pitch indictor and a left eye roll indicator; and
a right eye pitch selected from the group of a right eye pitch indicator and a right eye roll indicator;
whereby the person can receive visual inertial head orientation information for the left eye and the person can receive visual inertial head orientation information for the right eye.

8. The system of claim 1 wherein the indicator further comprises both a pitch indicator and a roll indicator.

9. The system of claim 8 wherein the pitch reference element comprises a line substantially parallel with the interaural axis.

10. The system of claim 8 wherein the pitch indicator comprises a pendulum and the roll indicator comprises a pendulum.

11. The system of claim 8 wherein the pitch indicator comprises a pendulum and the roll indicator comprises a rolling element.

12. The system of claim 8 wherein the pitch indicator and the roll indicator comprise a first fluid and a second fluid wherein:
the first fluid comprises a liquid; and
the first fluid has a higher density than the second fluid.

13. The system of claim 12 wherein the second fluid comprises a gas.

14. The system of claim 12 wherein the second fluid comprises a liquid.

15. The system of claim 12 wherein the first fluid comprises a translucent liquid.

16. The system of claim 12 wherein the first fluid comprises an opaque liquid.

17. The system of claim 12 wherein
the orientation reference symbol further comprises:
a left eye orientation reference symbol; and
a right eye orientation reference symbol;
the pitch indicator and the roll indicator further comprise:
a combined pitch and roll indicator for the left eye comprising a left visible fluid filled reservoir configured to be in a field of view of the person's left eye; and
a combined pitch and roll indicator for the right eye comprising a right visible fluid-filled reservoir configured to be in a field of view of the person's right eye; and
the system further comprises:
a left pitch reservoir configured to be located on the head of the person and behind the left visible fluid filled reservoir;
a right pitch reservoir configured to be located on the head of the person and behind the right visible fluid filled reservoir;
a fluid connection between a lower region of the left visible reservoir and a lower region of the left pitch reservoir;
a fluid connection between an upper region of the left visible reservoir and an upper region of the left pitch reservoir;
a fluid connection between a lower region of the right visible reservoir and a lower region of the right pitch reservoir; and
a fluid connection between an upper region of the right visible reservoir and an upper region of the right pitch reservoir.

18. The system of claim 17 wherein:
the left visible fluid filled reservoir is located in a region proximate to a bottom of the person's left eye field of view;
the right visible fluid filled reservoir is located in a region proximate to a bottom of the person's right eye field of view;
the left eye orientation reference symbol further comprises a horizontal line substantially parallel to the person's interaural axis; and
the right eye orientation reference symbol further comprises a horizontal line substantially parallel to the person's interaural axis.

* * * * *